(12) United States Patent
Laayoun et al.

(10) Patent No.: US 6,902,891 B2
(45) Date of Patent: Jun. 7, 2005

(54) PROCESS FOR LABELING A NUCLEIC ACID

(75) Inventors: Ali Laayoun, Lyons (FR); Lionel Menou, Lyons (FR); Christelle Tora, Lyons (FR); Aloke R. Banerjee, San Diego, CA (US); Michael M. Becker, San Diego, CA (US); Kenneth A. Browne, San Diego, CA (US); Matthew C. Friedenberg, San Diego, CA (US); Fred F. Hajjar, San Diego, CA (US)

(73) Assignees: Bio Merieux, Marcy l' Etoile (FR); Gen-Probe Incorporated, San Diego, CA (US)

( * ) Notice: Subject to any disclaimer, the term of this patent is extended or adjusted under 35 U.S.C. 154(b) by 312 days.

(21) Appl. No.: 09/736,151

(22) Filed: Dec. 15, 2000

(65) Prior Publication Data

US 2002/0081586 A1 Jun. 27, 2002

Related U.S. Application Data

(60) Provisional application No. 60/172,136, filed on Dec. 17, 1999.

(51) Int. Cl.$^7$ .............. C12Q 1/68; C12P 19/34; C07H 21/04; C07D 225/00; C07D 259/00
(52) U.S. Cl. .......... 435/6; 435/91.2; 536/25.3; 536/25.31; 540/465; 540/474; 556/1; 556/6
(58) Field of Search ............ 435/6, 91.2; 536/25.3, 536/25.31; 540/465, 474; 556/1, 6

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,786,600 A | 11/1988 | Kramer et al. | 435/235 |
| 4,800,159 A | 1/1989 | Mullis et al. | 435/172.3 |
| 4,868,105 A | 9/1989 | Urdea et al. | 435/6 |
| 5,124,246 A | 6/1992 | Urdea et al. | 435/6 |
| 5,130,238 A | 7/1992 | Malek et al. | 435/91 |
| 5,171,853 A | 12/1992 | Thorp et al. | 536/27 |
| 5,202,231 A | 4/1993 | Drmanac et al. | 432/6 |
| 5,317,098 A | 5/1994 | Shizuya et al. | 536/23.1 |
| 5,328,824 A | 7/1994 | Ward et al. | 435/6 |
| 5,399,491 A | 3/1995 | Kacian et al. | 435/91.21 |
| 5,407,797 A | 4/1995 | Marliere et al. | 435/6 |
| 5,422,252 A | 6/1995 | Walker et al. | 435/91.2 |
| 5,437,990 A | 8/1995 | Burg et al. | 435/91.21 |
| 5,445,934 A | 8/1995 | Fodor et al. | 435/6 |
| 5,449,767 A | 9/1995 | Ward et al. | 536/24.3 |
| 5,512,430 A | * 4/1996 | Gong | 435/5 |
| 5,525,464 A | 6/1996 | Drmanac et al. | 432/6 |
| 5,554,516 A | 9/1996 | Kacian et al. | 435/91.2 |
| 5,582,829 A | 12/1996 | Alliger et al. | 424/234.1 |
| 5,585,481 A | 12/1996 | Arnold, Jr. et al. | 536/25.33 |
| 5,605,796 A | 2/1997 | Chen et al. | 435/6 |
| 5,684,149 A | 11/1997 | Morrow | 540/474 |
| 5,688,670 A | 11/1997 | Szostak et al. | 435/91.21 |
| 5,700,637 A | 12/1997 | Southern | 435/6 |
| 5,744,305 A | 4/1998 | Fodor et al. | 435/6 |
| 5,766,849 A | 6/1998 | McDonough et al. | 435/6 |
| 5,807,522 A | 9/1998 | Brown et al. | 422/50 |
| 5,981,734 A | * 11/1999 | Mirzabekov | 536/25.3 |
| 5,989,904 A | 11/1999 | Das et al. | 435/320.1 |
| 6,297,010 B1 | * 10/2001 | Stefano | 435/6 |
| 6,376,179 B1 | * 4/2002 | Laayoun | 435/6 |

FOREIGN PATENT DOCUMENTS

| | | | |
|---|---|---|---|
| DE | A 3 910 151 | 10/1990 | C12P/19/34 |
| DE | 198 15 864 A1 | 10/1999 | C07H/19/20 |
| EP | A 0 063 879 | 11/1982 | C07H/19/00 |
| EP | A 0 097 373 | 1/1984 | C07H/21/00 |
| EP | A 0 280 058 | 8/1988 | H04N/9/82 |
| EP | A 0 286 898 | 10/1988 | C07H/21/00 |
| EP | A 0 302 175 | 2/1989 | C07H/21/00 |
| EP | A 0 320 308 | 6/1989 | C12Q/1/68 |
| EP | A 0 329 198 | 8/1989 | C07H/19/10 |
| EP | A 0 567 841 | 11/1993 | C07H/19/04 |
| EP | A 0 709 468 | 5/1996 | C12Q/1/68 |
| EP | 0 801 072 A | 10/1997 | C07H/21/02 |
| FR | 2 768 743 | 3/1999 | C12N/1/06 |
| FR | 2 781 500 | 1/2000 | C12N/1/06 |
| WO | WO A 88/01302 | 2/1988 | C12Q/1/68 |
| WO | WO A 88/04300 | 6/1988 | C07H/17/02 |
| WO | WO A 88/10315 | 12/1988 | C12Q/1/68 |
| WO | WO A 90/14439 | 11/1990 | C12Q/1/64 |
| WO | WO A 93/16094 | 8/1993 | C07H/21/00 |
| WO | WO 93/20241 | 10/1993 | C12Q/1/68 |
| WO | WO A 93/22461 | 11/1993 | C12Q/1/68 |
| WO | WO A 94/03472 | 2/1994 | C07H/21/04 |
| WO | WO A 94/29723 | 12/1994 | G01N/33/547 |
| WO | WO A 95/03142 | 2/1995 | B09B/1/00 |
| WO | WO A 95/03430 | 2/1995 | C12Q/1/68 |
| WO | WO A 95/08000 | 3/1995 | C12Q/1/68 |
| WO | WO A 95/11995 | 5/1995 | C12Q/1/68 |
| WO | WO A 96/19729 | 6/1996 | G01N/33/53 |
| WO | WO A 96/28460 | 9/1996 | C07H/21/00 |
| WO | WO A 98/05766 | 2/1998 | C12N/15/10 |
| WO | WO A 98/11104 | 3/1998 | C07D/405/04 |
| WO | WO 98/27229 | 6/1998 | C12Q/1/68 |
| WO | WO 99/65926 | 12/1999 | C07H/21/00 |

OTHER PUBLICATIONS

Chee, M. et al., "Accessing Genetic Information with High–Density DNA Arrays," Science, vol. 274, pp. 610–614, 1996.

(Continued)

*Primary Examiner*—Kenneth R. Horlick
*Assistant Examiner*—Joyce Tung
(74) *Attorney, Agent, or Firm*—Oliff & Berridge, PLC

(57) ABSTRACT

A process of fragmenting and labeling a synthetic or natural nucleic acid, comprising the steps of providing a mixture containing a nucleic acid, a labeling agent containing a detectable label, and at least one multivalent metal cation in a substantially aqueous solution; chemically fragmenting the nucleic acid in the mixture to produce a multiplicity of nucleic acid fragments; and attaching at least one label to at least one of the nucleic acid fragments to produce a detectably labeled nucleic acid fragment.

49 Claims, No Drawings

OTHER PUBLICATIONS

Caviani Pease, A. et al., "Light–generated oligonucleotide arrays for rapid DNA sequence analysis," Proc. Natl. Acad. Sci. USA, vol. 91, pp. 5022–5026, 1994.

Sambrook, J. et al., "Molecular Cloning, a Laboratory Manual," Cold Spring Harbor Laboratory Press, Second Edition, pp. 5.30–5.95, 1989.

Lindahl, T. et al., "Rate of Chain Breakage at Apurinic Sites in Double–Stranded Deoxyribonucleic Acid," Biochemistry, vol. 11, No. 19, pp. 3618–3623, 1972.

Liuzzi, M. et al., "Characterization of damage in γ–irradiated and $OsO_4$–treated DNA using methoxyamine," Int. J. Radiat. Biol., vol. 54, No. 5, pp. 709–722, 1988.

Breslow, R. et al., "Recognition and catalysis in nucleic acid chemistry," Proc. Natl. Acad. Sci. USA, vol. 90, pp. 1201–1207, 1993.

Hovinen, J. et al., "Imidazole Tethered Oligodeoxyribonucleotides: Synthesis and RNA Cleaving Activity," J. Org. Chem., vol. 60, pp. 2205–2209, 1995.

Blattner, F. et al., "The Complete Genome Sequence of *Escherichia coli* K–12," Science, vol. 277, pp. 1453–1462, 1997.

Abravaya, K. et al., "Strategies to Avoid Amplicon Contamination," Nucleic Acid Amplification Technologies, pp. 125–133, 1997.

Chevalier, J. et al., "Biotin and Digoxigenin as Labels for Light and Electron Microscopy in Situ Hybridization Probes: Where Do We Stand?" J. Histochem. Cytochem., vol. 45, No. 4, pp. 481–491, 1997.

Greisen, K. et al., "PCR Primers and Probes for the 16S rRNA Gene of Most Species of Pathogenic Bacteria, Including Bacteria Found in Cerebrospinal Fluid," J. Clinical Microbiol., vol. 32, No. 2, pp. 335–351, 1994.

Troesch, A. et al., "*Mycobacterium* Species Identification and Rifampin Resistance Testing with High–Density DNA Probe Arrays," J. Clinical Microbiol., vol. 37, No. 1, pp. 49–55, 1999.

Furuta, T. et al., "Direct Esterification of Phosphates with Various Halides and its Application to Synthesis of cAMP Alkyl Triesters," J. Chem. Soc. Perkin Trans., vol. 1, pp. 3139–3142, 1993.

Sambrook, J. et al., "Removal of Ethidium Bromide from DNAs Purified by Equilibrium Centrifugation in CsCl–Ethidium Bromide Gradients," Plasmid Vectors, $2^{nd}$ Edition, p. 1.46, 1989.

Zuckermann, R. et al., "Site–selective cleavage of structured RNA by a staphylococcal nuclease–DNA hybrid," Proc. Natl. Acad. Sci. USA, vol. 86, pp. 1766–1770, 1989.

Gish, G. et al., "DNA and RNA Sequence Determination Based on Phosphorothioate Chemistry," Science, vol. 240, pp. 1520–1522, 1988.

Nakamaye, K.L. et al., "Direct sequencing of polymerase chain reaction amplified DNA fragments through the incorporation of deoxynucleoside α–thiotriphosphates," Nucleic Acids Res., vol. 16, No. 21, pp. 9947–9959, 1988.

Ruffner, D.E. et al., "Thiophosphate interference experiments locate phosphates important for the hammerhead RNA self–cleavage reaction," Nucleic Acids Res., vol. 18, No. 20, pp. 6025–6029, 1990.

Almer, H. et al., "Nonenzymatic Hydrolysis of an RNA–dimer Containing a Thiophosphate Linkage," Nucleosides & Nucleotides, vol. 10, pp. 653–655, 1991.

Mag, M. et al., "Synthesis and selective cleavage of an oligodeoxynucleotide containing a bridged internucleotide 5'–phosphorothioate linkage," Nucleic Acids Res., vol. 19, No. 7, pp. 1437–1441, 1991.

Vyle, J.S. et al, "Sequence– and Strand–Specific Cleavage in Oligodeoxyribonucleotides and DNA Containing 3'–Thiothymidine," Biochemistry, vol. 31, pp. 3012–3018, 1992.

Podyminogin, M.A. et al., "Synthetic RNA–cleaving molecules mimicking ribonuclease A active center. Design and cleavage of tRNA transcripts," Nucleic Acids Res., vol. 21, No. 25, pp. 5950–5956, 1993.

Kuimelis, R.G. et al., "Cleavage properties of an oligonucleotide containing a bridged internucleotide 5'–phosphorothioate RNA linkage," Nucleic Acids Res., vol. 23, No. 23, pp. 4753–4760, 1995.

Fidanza, J.A. et al., "Site–Specific Labeling of DNA Sequences Containing Phosphorothioate Diesters," J. Am. Chem. Soc., vol. 114, pp. 5509–5517, 1992.

Vlassov, V.V. et al., "Cleavage of tRNA with imidazole and spermine imidazole constructs: a new approach for probing RNA structure," Nucleic Acids Res., vol. 23, No. 16, pp. 3161–3167, 1995.

Ramsay, G., "DNA chips: State–of–the–art," Nature Biotechnol., vol. 16, pp. 40–44, 1998.

Ginot, F., "Oligonucleotide Micro–Arrays for Identification of Unknown Mutations: How Far from Reality?" Human Mutation, vol. 10, pp. 1–10, 1997.

Cheng, J. et al., "Microchip–based Devices for Molecular Diagnosis of Genetic Diseases," Molec. Diagnosis, vol. 1, No. 3, pp. 183–200, 1996.

Livache, T. et al., "Preparation of a DNA matrix via an electrochemically directed copolymerization of pyrrole and oligonucleotides bearing a pyrrole group," Nucleic Acids Res., vol. 22, No. 15, pp. 2915–2921, 1994.

Wrzesinski, J. et al., "Specific RNA cleavages induced by manganese ions," FEBS Letters, vol. 374, pp. 62–68, 1995.

Moss, R.A. et al., "Remarkable acceleration of dimethyl phosphate hydrolysis by ceric cations," Chem. Commun., pp. 1871–1872, 1998.

Roelfes, G. et al., "Efficient DNA Cleavage with an Iron Complex without Added Reductant," J. Am. Chem. Soc., vol. 122, pp. 11517–11518, 2000.

Hodges, R.R. et al., "'Post–Assay' Covalent Labeling of Phosphorothioate–Containing Nucleic Acids with Multiple Fluorescent Markers," Biochemistry, vol. 28, pp. 261–267, 1989.

Fidanza, J.A. et al., "Introduction of Reporter Groups at Specific Sites in DNA Containing Phosphorothioate Diesters," J. Am. Chem. Soc., vol. 111, pp. 9117–9119, 1989.

Cheng, J. et al., "Preparation and hybridization analysis of DNA/RNA from *E. coli* on microfabricated bioelectronic chips," Nature Biotechnol., vol. 16, pp. 541–546, 1998.

Trawick, B.N. et al., "Inorganic Mimics of Ribonucleases and Ribozymes: From Random Cleavage to Sequence–Specific Chemistry to Catalytic Antisense Drugs," Chem. Rev., vol. 98, pp. 939–960, 1998.

Oivanen, M. et al., "Kinetics and Mechanisms for the Cleavage and Isomerization of the Phosphodiester Bonds of RNA by Bronsted Acids and Bases," Chem. Rev., vol. 98, pp. 961–990, 1998.

Longo, M.C. et al., "Use of uracil DNA glycosylase to control carry–over contamination in polymerase chain reactions," Gene, vol. 93, pp. 125–128, 1990.

Walker, G.T. et al., "Isothermal in vitro amplification of DNA by a restriction enzyme/DNA polymerase system," Proc. Natl. Acad. Sci. USA, vol. 89, pp. 392–396, 1992.

Bibillo, A. et al., "The non–enzymatic hydrolysis of oligoribonucleotides VI. The role of biogenic polyamines," Nucleic Acids Res., vol. 27, No. 19, pp. 3931–3937, 1999.

Sentagne, C. et al., "DNA cleavage photoinduced by new water–soluble zinc porphyrins linked to 9–methoxyellipticine," J. Photochem. Photobiol. B., vol. 16, pp. 47–59, 1992.

Nadji, S. et al., "Photochemically and Photoenzymatically Cleavable DNA," J. Am. Chem. Soc., vol. 114, pp. 9266–9269, 1992.

Povsic, T.J. et al., "Sequence–Specific Alkylation of Double– Helical DNA by Oligonucleotide–Directed Triple–Helix Formation," J. Am. Chem. Soc., vol. 112, pp. 9428–9430, 1990.

Kozal, M.J., "Extensive polymorphisms observed in HIV–I clade B protease gene using high–density oligonucleotide arrays," Nature Med., vol. 2, No. 7, pp. 753–759, 1996.

* cited by examiner

SEQUENCE LISTING

<160> NUMBER OF SEQ ID NOS: 11

<210> SEQ ID NO 1
<211> LENGTH: 43
<212> TYPE: DNA
<213> ORGANISM: HIV

<400> SEQUENCE: 1
aattaaccct cactaaaggg agacagagcc aacagcccca cca         43

<210> SEQ ID NO 2
<211> LENGTH: 54
<212> TYPE: DNA
<213> ORGANISM: HIV

<400> SEQUENCE: 2
taatacgact cactataggg agatttcccc actaacttct gtatgtcatt gaca         54

<210> SEQ ID NO 3
<211> LENGTH: 49
<212> TYPE: DNA
<213> ORGANISM: HIV

<400> SEQUENCE: 3
taatacgact cactataggg agagggccat ccattcctgg ctttaattt         49

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 4
gctcgttgcg ggacttaacc caacat         26

```
<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:primer ; the
      phosphate between nucleotides at positions 16 and 17 is a
      thiophosphate

<400> SEQUENCE: 5
gctcgttgcg ggacttaacc caacat                                         26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:primer ; the
      phosphate at the 3' end is a terminal thiophosphate

<400> SEQUENCE: 6
gctcgttgcg ggacttaacc caacat                                         26

<210> SEQ ID NO 7
<211> LENGTH: 26
<212> TYPE: RNA
<213> ORGANISM: Artificial Sequence
<220> FEATURE:
<223> OTHER INFORMATION: Description of Artificial Sequence:primer ; the
      phosphate between the two nucleotides at position
      16 and 17 is a thiophosphate

<400> SEQUENCE: 7
gcucguugcg ggacuuaacc caacau                                         26

<210> SEQ ID NO 8
<211> LENGTH: 26
<212> TYPE: RNA
<213> ORGANISM: Artificial Sequence
<220> FEATURE:
<223> OTHER INFORMATION: Description of Artificial Sequence:primer ; the
      phosphate at the 3' end is a terminal
      thiophosphate

<400> SEQUENCE: 8
gcucguugcg ggacuuaacc caacau                                         26

<210> SEQ ID NO 9
<211> LENGTH: 26
<212> TYPE: RNA
<213> ORGANISM: Artificial Sequence
<220> FEATURE:
<223> OTHER INFORMATION: Description of Artificial Sequence:primer

<400> SEQUENCE: 9
gcucguugcg ggacuuaacc caacau                                         26

<210> SEQ ID NO 10
<211> LENGTH: 16
<212> TYPE: RNA
<213> ORGANISM: Artificial Sequence
<220> FEATURE:
<223> OTHER INFORMATION: Description of Artificial Sequence:primer

<400> SEQUENCE: 10
gcucguugcg ggacuu                                                    16
```

```
<210> SEQ ID NO 11
<211> LENGTH: 16
<212> TYPE: RNA
<213> ORGANISM: Artificial Sequence
<220> FEATURE:
<223> OTHER INFORMATION: Description of Artificial Sequence:primer ; the
      phosphate at the 3' end is a terminal thiophosphate

<400> SEQUENCE: 11
gcucguugcg ggacuu                                                      16
```

PROCESS FOR LABELING A NUCLEIC ACID

FIELD OF THE INVENTION

The present invention relates to a novel process for labeling a nucleic acid, and particularly relates to a chemical method for simultaneously fragmenting and labeling nucleic acids.

BACKGROUND

There are a large number of methods for labeling nucleotides, oligonucleotides or nucleic acids (herein referred to by the term polynucleotides). Polynucleotides can be labeled either during synthesis (e.g., by incorporating at least one labeled nucleotide) or by adding a label to the polynucleotide after synthesis. For example, one method attaches the label to the base, whether the latter is a natural base or a modified base. A second method attaches the label to the sugar, again whether it is a natural sugar or a modified sugar. A third method attaches the label to the phosphate. Often, preferred methods attach the label to the base or to the sugar, because such methods are more convenient and provide more options for labeling. See, for example, the methods disclosed in EP-A-0.329.198, EP-A-0.302.175, EP-A-0.097.373, EP-A-0.063.879, U.S. Pat. No. 5,449,767, U.S. Pat. No. 5,328,824, WO-A-93/16094, DE-A-3.910.151 and EP-A-0.567.841 in the case of base labeling, or EP-A-0.286.898 in the case of sugar labeling. Attaching the label to the phosphate is more complex because nucleic acids are water soluble and the reactivity of the phosphate in an aqueous solution is low. Nonetheless, phosphate labeling methods have been described in EP-A-0.280.058. In this method, the label is attached to the phosphate, which is attached to the sugar in the 3' and/or 5' positions, for a deoxyribonucleotide, and in the 2', 3' and/or 5' positions for a ribonucleotide. The labeled nucleotide may be incorporated into the polynucleotide or oligonucleotide during synthesis.

However, the labeling described in EP-A-0.280.058 does not uniformly label the nucleic acids. The incorporation of the labeled nucleotides into the polynucleotides cannot be controlled and depends on the composition of synthesized polynucleotides. Thus, some polynucleotides may contain a large number of labeled nucleotides whereas others may not contain any. As a result, the intensity of the signal emitted by these labeled nucleic acids will not be uniform, making it difficult to interpret the results when detecting the nucleic acids.

Another method, described in U.S. Pat. No. 5,317,098 relates to nucleic acids (e.g., 15-mers) which are labeled at their 5' ends by using imidazole and a linker arm. Furthermore, phosphate is added to nucleic acids by using a kinase, thus adding at least one additional step. When this method is used to label larger nucleic acids, the specific activity is low because this technique labels only the 5' end.

In some instances, fragmentation of a labeled nucleic acid is also desirable, such as to increase hybridization kinetics of the labeled fragment with another nucleic acid by decreasing the size of the labeled polynucleotide. In contrast, hybridization using a larger labeled polynucleotide may result in a quantitative and qualitative loss of the signal. Fragmentation of a labeled polynucleotide may also be needed to reduce steric hindrance.

Steric hindrance may result from the length of the nucleic acid and the existence of secondary structures. Fragmentation helps to remove these structures and, thus, optimize hybridization. Steric hindrance plays a particularly important role in hybridization to surfaces which contain a high density of capture probes, for example, in high-density arrays of probes as occur on "DNA chips" (GENECHIP®; Affymetrix, Santa Clara, Calif., USA; (Chee et al., 1996, Science 274:610–614; Caviani Pease et al., 1994, Proc. Natl. Acad. Sci. USA 91:5022–5026; U.S. Pat. No. 5,445,934; U.S. Pat. No. 5,744,305; Ramsay, 1998, Nature Biotechnol. 16:40–44, Ginot, 1997, Human Mutation 10:1–10; Cheng et al., 1996, Molec. Diagnosis 1(3).183–200; Livache et al., 1994, Nucl. Acids Res. 22(15): 2915–2921; Cheng et al., 1998, Nature Biotechnol. 16. 541–546; U.S. Pat. No. 5,525, 464, U.S. Pat. No. 5,202,231, U.S. Pat. No. 5,807,522 and U.S. Pat. No. 5,700,637).

Methods for fragmenting nucleic acids are known in the art. For example, fragmentation can be enzymatic (i.e. by nucleases such as DNases or RNases). This generates small fragments having 3'-OH, 5'-OH, 3'-phosphate and 5'-phosphate ends. Alternatively, fragmentation can be chemical. For example, for DNA, it is possible to depurinate or depyrimidinate the DNA, which are then fragmented in the presence of a base (i.e., "β-elimination") DNA can be fragmented by oxidation, alkylation or free radical addition mechanisms. Metal cations, which are often combined with organic molecules which may function as chemical catalysts, for example imidazole, are used for fragmenting RNA. This fragmentation is preferably carried out in an alkaline medium and generates fragments having 3'-phosphate ends.

Different nucleic acid fragmentation techniques have been described in Trawick et al., 1998, Chem Rev. 98; 939–960 and Oivanen at al., 1998, Chem Rev. 98: 961–990.

A method for fragmenting and labeling RNA is described in WO-A-88/04300, in which the fragmentation is carried out using RNA which possesses enzymatic properties (ribozymes). Fragmentation by ribozymes releases a nucleic acid (5') HO end and a nucleic acid (3') HO-PO$_2$ end. Radioactive labeling is then effected by incorporating a radioactive phosphate, derived from GTP, at the 5'OH end; no phosphate resulting from fragmentation is used in labeling. Fragmentation carried out by ribozymes implies specificity between the ribozymes and the target nucleic acids to be cleaved, after which the phosphate acts as the label.

Reliable diagnostic tests based on nucleic acid amplification techniques often include steps to control contamination by nucleic acids that can otherwise serve as targets for further amplification. Several decontamination procedures have been developed (Longo et al., 1990, Gen. 93: 125–128; Abravaya et al., in *Nucleic Acid Amplification Technologies*, p 125–133, (1997) Eds. Lee et al. (Eaton Publishing 1997) at pp. 125–133; EP 0 709 468 A1 and U.S. Pat. No. 5,605,796). These procedures make the amplified nucleic acid product incapable of being a target for further amplification, generally by degrading nucleic acids that would otherwise serve as targets (e.g., by using irradiation, endonucleases, uracil DNA glycosylase, primer modification or photochemical methods). Some of these methods are difficult to implement, are inefficient or introduce additional steps and/or toxic compounds into a procedure (e.g., UV inactivation, photochemical degradation, primer modification). Enzymatic methods use enzymes that are often expensive and incompatible with amplification and/or detection buffers. Thus, there remains a need for efficient and convenient methods of target nucleic acid removal.

SUMMARY OF THE INVENTION

One aspect of the present invention is a process of fragmenting and labeling a synthetic or natural nucleic acid, comprising the steps of providing a mixture containing a nucleic acid, a labeling agent containing a detectable label, and at least one multivalent metal cation in a substantially aqueous solution; chemically fragmenting the nucleic acid in the mixture to produce a multiplicity of nucleic acid fragments, and attaching at least one label to at least one of the nucleic acid fragments to produce a detectably labeled nucleic acid fragment. In one embodiment of the process the nucleic acid is DNA, RNA, a chimeric DNA-RNA polymer, DNA comprising at least one thiophosphate nucleotide or RNA comprising at least one thiophosphate nucleotide. In another embodiment, reagents used in the fragmenting and attaching steps are added to an in vitro nucleic acid amplification mixture. According to yet another embodiment, the at least one label is attached lo at least one phosphate of the nucleic acid fragments, The process may further comprise the step of treating the mixture after the fragmenting and attaching steps to decrease or eliminate unattached labeling agent. In one embodiment, the treating step consists in adding a quencher to the mixture after the fragmenting and attaching steps. Preferred quenchers include a pyrophosphate, thiol derivative, chelating agent, phosphate anion or carbonate anion. In another embodiment, the treating step physically separates the labeled nucleic acid fragment from unattached labeling agent in the mixture after the fragmenting and attaching steps. The treating step may further include adding an acid to the mixture after the fragmenting and attaching steps. Another embodiment of the treating step further includes adding a chelating agent to the mixture after the fragmenting and attaching steps. In one embodiment, the treating step uses an organic solvent to separate the labeled nucleic acid fragment from the unattached labeling agent. Preferred organic solvents are 1-butanol, 2-butanol, isopentyl alcohol, 1-pentanol or cyclohexanol. In another embodiment, the treating step separates the labeled nucleic acid fragment from the unattached labeling agent by using solid phase extraction of the nucleic acid fragments on a solid support. Preferably, the solid support is beads, gels, ion exchange resin, reverse phase resin, silica matrix or a membrane. In another embodiment, the labeled nucleic acid fragment is eluted from the solid support by using a buffer containing betaine. One embodiment includes a treating step that precipitates the labeled nucleic acid fragments at ambient temperature from a solution that contains betaine, DTAB and unlabeled nucleic acid. Another embodiment uses a treating step that dilutes an in vitro nucleic acid amplification mixture. In one embodiment, the fragmenting and attaching steps are performed in a single reaction mixture, whereas in another embodiment, the fragmenting and attaching steps are effected in separate steps In preferred embodiments, the attaching step attaches a label to an internal or terminal thiophosphate or to an internal or terminal phosphate. In one embodiment, the fragmenting step further includes use of a chemical catalyst. Preferably, the chemical catalyst is a general base selected from the group consisting of imidazole, a substituted analogue of imidazole, and a compound that includes an imidazole ring or substituted analogue of an imidazole ring. Preferred chemical catalysts are selected from the group consisting of N-methylimidazole, MOPS, HEMS, PIPES, and bioorganic polyamines. In preferred embodiments of the process, the nucleic acid is an RNA or RNA comprising at least one thiophosphate nucleotide, and the multivalent metal cation is $Mg^{2+}$, $Sr^{2+}$, $Ba^{2+}$, $Pb^{2+}$, $Zn^{2+}$, $Cd^{2+}$, $Mn^{2+}$, $Fe^{2+}$, $Co^{2+}$, $Ni^{2+}$, $Ru^{3+}$, $Ce^{3+}$, $Eu^{3+}$, $Tb^{3+}$, $Tm^{3+}$, $Yb^{3+}$ or $Lu^{3+}$. In another preferred embodiment, the nucleic acid is a DNA and the multivalent metal cation is $Tb^{3+}$. In one embodiment, the nucleic acid is RNA or RNA comprising at least one thiophosphate nucleotide, and the multivalent metal cation is $Mn^{2+}$, $Cr^{3+}$, $Ce^{3+}$, $Yb^{3+}$, $Tb^{3+}$, $Eu^{2+}$, $Zn^{2+}$ or $Pb^{2+}$. In another embodiment the nucleic acid is DNA or DNA comprising at least one thiophosphate nucleotide, and the multivalent metal cation is $Mn^{2+}$, $Zn^{2+}$, $Be^{2+}$, $Cr^{3+}$, $Pb^{2+}$, $In^{3+}$, $Tb^{3+}$, $Ce^{3+}$, $Yb^{3+}$ or $Ni^{2+}$. Preferred embodiments of the process use a multivalent metal cation that is $Mn^{2+}$, $Zn^{2+}$, $Tb^{3+}$ or $Ce^{3+}$. In preferred embodiments, the mixture contains the labeling agent in a concentration of between 0.1 mM to 4 mM, more preferably between 0.1 mM to 1 mM. In preferred embodiments, the labeling agent is between 0.3 mM to 0.55 mM. Preferably, the mixture contains a labeling agent that contains alkyl halide or haloacetamide reactive functions. Preferred labeling agents arc 5-(bromomethyl) fluorescein, 6-(bromomethyl)fluorescein, 6-iodoacetamidofluorescein or 5-iodoacetamidofluorescein.

DETAILED DESCRIPTION OF THE INVENTION

The present invention includes methods to chemically fragment nucleic acids and simultaneously label the fragments with a detectable label, such as a fluorescent compound. The labeled fragments can then be detected by a variety of methods. This process is useful for preparing labeled nucleic acids, such as fragments to be bound to immobilized probes or detection probes. This process can limit nonspecific signals that result from the labeling step, particularly when combined with nucleic acid purification steps using any of a variety of methods. Furthermore, this process provides nucleic acid fragments that are relatively uniformly labeled. The fragmentation process results in fragments that are of an optimum size for hybridization to nucleic acid probes used in detection of the fragmented nucleic acids, thus making the detecting step more rapid and efficient.

The present invention relates to a process for labeling a synthetic or natural nucleic acid, characterized by the steps of fragmenting a nucleic acid by chemical processes and attaching a label to the fragmented nucleic acid. The process may optionally include treating the labeling mixture to decrease the amount of labeling agent therein.

By "nucleic acid" is meant DNA, RNA or chimeric DNA-RNA polymers (single-stranded, double-stranded or partially double-stranded), and nucleic acid molecules made partially or completely of nucleotide analogues or a basic residues that may be present in the sequence. The DNA or RNA may be purified from a natural source (e.g., extracted from a cell) or be synthetically prepared (e.g., by chemical enzymatic or other known synthesis methods). In some embodiments, the nucleic acid is amplified DNA, amplified RNA, or a mixture thereof which may further include at east one thiophosphate nucleotide. A phosphate may be a terminal phosphate which is located at the 3' end and/or the 5' end of the nucleic acid fragments, an internal phosphate or an internal thiophosphate.

The term nucleic acid includes conventional RNA and DNA, as well as analogs thereof. The "backbone" of a nucleic acid may be made up of a variety of linkages known in the art, including one or more of sugar-phosphodiester linkages, peptide-nucleic acid bonds (sometimes referred to as "peptide nucleic acids" as described by Hydig-Hielsen et al., PCT Pat. App. No. WO 95/32305), phosphorothioate linkages, methylphosphonate linkages or combinations thereof. Sugar moieties of the nucleic acid may be either ribose or deoxyribose, or similar compounds having known substitutions, such as, for example, 2' methoxy substitutions and 2' halide substitutions (e.g., 2'-F). The nitrogenous bases may be conventional bases (A, G, C. T, U), known analogs thereof (e.g., inosine or "I"; see *The Biochemistry of the Nucleic Acids* 5–36, Adams et al., ed., 11$^{th}$ ed, 1992), known derivatives of purine or pyrimidine bases (e.g., N$^4$-methyl deoxygaunosine, deaza- or aza-purines and dea- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines; see, Cook, PCT Pat. App. No. WO 93/13121) and "abasic" residues where the backbone includes no nitrogenous base for one or more residues of the polymer (U.S. Pat. No. 5,585,481). A nucleic acid may comprise only conventional sugars, bases and linkages found in RNA and DNA, or may include both conventional components and substitutions (e.g., conventional bases linked via a methoxy backbone, or a nucleic acid including conventional bases and one or more base analogs).

By "amplification" is meant any known procedure for obtaining multiple copies of a target nucleic acid sequence or its complement or fragments thereof Known amplification methods include, for example, transcription-mediated amplification, replicase-mediated amplification, polymerase chain reaction (PCR) amplification, ligase chain reaction (LCR) amplification and strand-displacement amplification (SDA). Replicas mediated amplification uses self-replicating RNA molecules, and a replicase such as QB-replicase (U.S. Pat. No. 4,786,600; PCT Pat. App. No. WO 90/14439). PCR amplification is well known and uses DNA polymerase, primers and thermal cycling to synthesize multiple copies of the two complementary strands of DNA or cDNA (e.g., see U.S. Pat. Nos. 4,683,195, 4,683,202, and 4,800,159; *Methods in Enzymology*, 1987, Vol. 155: 335–350). LCR amplification uses at least four separate oligonucleotides to amplify a target and its complementary strand by using multiple cycles of hybridization, ligation, and denaturation (EP Pat. App. Pub. No. 0 320 308). SDA is a method in which a primer contains a recognition site for a restriction endonuclease such that the endonuclease will nick one strand of a hemimodified DNA duplex that includes the target sequence, followed by amplification in a series of primer extension and strand displacement steps (Walker et al., 1992, Proc. Natl. Acad. Sci. USA 89:392–396; and U.S. Pat. No. 5,422,252). Transcription-associated amplification is a preferred embodiment of the present invention. It will, however, be apparent to one skilled in the art that the methods of the present invention can be readily used with nucleic acid amplified by any method.

By "transcription-mediated amplification" or "transcription-associated amplification" is meant any type of nucleic acid amplification that uses an RNA polymerase to produce multiple RNA transcripts from a nucleic acid template (see U.S. Pat. Nos. 4,868,105 and 5,124,246, 5,130, 238, 5,399,491 and 5,554,516, 5,437,990; and PCT Application Nos. WO 93/22461, WO 88/01302 and WO 88/10315, WO 94/03472 and WO 95/03430. Transcription-associated amplification generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Preferred methods of transcription-mediated amplification (TMA) are disclosed in detail in U.S. Pat. Nos. 5,399,491 and 5,554,516 and PCT Application Nos. WO 93/22461, WO 94/03472 and WO 95/03430.

Chemical fragmentation of the nucleic acid is carried out by using at least one multivalent metal cation, which may or may not be combined with a chemical catalyst. Preferred multivalent metal cations include divalent and trivalent cations, lanthanides, Group IIA, Group IV and transition metals (e.g., Mn$^{2+}$, Mg$^{2+}$, Sr$^{2+}$, Ba$^{2+}$, Pb$^{2+}$, Zn$^{2+}$, Cd$^{2+}$, Fe$^{2+}$, Co$^{2+}$, Ni$^{2+}$, Cr$^{3+}$, Ce$^{3+}$, Eu$^{3+}$, Lu$^{3+}$, Ru$^{3+}$, Tb$^{3+}$, Tm$^{3+}$ and Yb$^{3+}$) or combinations thereof. Both fragmentation and labeling may be performed in the presence of at least one multivalent metal cation, such as Mn$^{2+}$, Zn$^{2+}$ or Pb$^{2+}$, or lanthanide cation, such as Tb$^{3+}$ or Ce$^{3+}$. Chemical catalysts used in the fragmentation process are those that act as a general base, including, for example, imidazole, a substituted analogue (e.g., N-methylimidazole), or a chemical compound that includes an imidazole ring or a substituted analogue thereof Additional chemical catalysts that may be used for nucleic acid fragmentation include MOPS, HEPES, PIPES, and bioorganic polyamines, such as spermine, spermidine and putrescine (Bibille et al., 1999, Nucleic Acids Res. 27: 3931–3937).

In preferred methods of the present invention, the nucleic acid to be fragmented is RNA and the multivalent metal cation is at least one of Mn$^{2+}$, Mg$^{2+}$, Sr$^{2+}$, Ba$^{2+}$, Pb$^{2+}$, Zn$^{2+}$, Cd$^{2+}$, Fe$^{2+}$, Co$^{2+}$, Ni$^{2+}$, Ru$^{3+}$, Ce$^{3+}$, Eu$^{3+}$, Lu$^{3+}$, Tb$^{3+}$, Tm$^{3+}$ or Yb$^{3+}$. In other embodiments in which RNA is fragmented, the preferred multivalent metal cation is at least one of Mn$^{2+}$, Zn$^{2+}$, Eu$^{2+}$, Pb$^{2+}$, Ce$^{3+}$, Cr$^{3+}$, Tb$^{3+}$ or Yb$^{3+}$.

In preferred methods of the present invention, the nucleic acid to be fragmented is DNA and the multivalent metal cation is at least one of 2, Zn$^{2+}$, Be$^{2+}$, Pb$^{2+}$, Ni$^{2+}$, Cr$^{3+}$, Ce$^{3+}$, Eu$^{3+}$, In$^{3+}$, Tb$^{3+}$ or Yb$^{3+}$. In another preferred embodiment, the nucleic acid to be fragmented is DNA that includes at least one thiophosphate nucleotide, and the metal cation is Tb$^{3+}$.

Additional chemical fragmentation of DNA that optionally contains at least one thiophosphate nucleotide may be effected by using metal chelating agents (Sentagne et al., 1992, J. Photochem. Photobiol. B. 16; 47–59), photoactivatable compounds (Nadji, 1992, Am. Chem. Soc. 112: 9266–9269) and alkylating agents (Povsic et al., 1990, J. Am. Chem. Soc. 112: 9428–9430).

By "labeling" is meant attachment of a detectable label to a nucleic acid to generate a detectable signal associated with the nucleic acid. The compound which comprises the label is the labeling agent Known labels include enzymes (e.g., alkaline phosphatase) that produce a signal e.g., by colorimetry, fluorescence, luminescence; chromophores (e.g., fluorescent and luminescent compounds and dyes); electron dense groups that are detectable by electron microscopy or by measuring electrical properties; size-dependent detectable groups that can be detected using optical or physical methods; and radionuclides.

Labeling agents of the present invention include compounds that include alkyl halide (e.g., bromoalkyl or bromomethyl) and haloacetamide reactive functions (e.g., iodoacetamido group). Such labeling agents include, for example, 5-(bromomethyl)fluorescein, 6-(bromomethyl) fluorescein, 6-iodoacetamidofluorescein and 5-iodoacetamidofluorescein. Those skilled in the art will appreciate that other reactive compounds may equivlantly be used based on their known chemical reactivity, such as, for example, hydrazine, alkoxylamine, alkyl or aryl halides and maleimide. Preferred concentrations of the labeling agent are in the range having a lower limit of 0.01 mM and an upper limit of 10 mM, more preferably in a range having a lower limit of 0.1 mM and an upper limit of 4 mM. In some preferred embodiments, the labeling agent is used in a concentration range of between 0.1 mM to 1 mM and in other embodiments in a concentration range of between 0.3 mM to 0.55 mM When the labeling agent is 5-(bromomethyl)fluorescein, the fragmentation and labeling steps preferably occur in the presence of $Mn^{2+}$ at 15 mM to 60 mM, imidazole in a range between 5 mM to 30 mM and at pH in a range between 6.8 and 7.2. In one embodiment of the present invention, nucleic acid fragmentation and labeling are effected in one reaction mixture, additionally providing a method for target inactivation, eliminating the need for a post-detection step of removing any remaining target nucleic acid. For example, an RNA target molecule present in the fragmentation and labeling reaction mixture would be degraded into short fragments.

An advantage of the present invention is that nucleic acid fragmentation and labeling reaction also serves as a decontamination tool. That is, the process fragments RNA molecules present in the amplification mixture thus removing potential targets for further amplification from the system because the fragmented RNA fragments are incapable of being a target for further amplification.

In another embodiment of the present invention fragmentation and labeling are effected in two steps, using either the entire volume of amplification reaction or a portion thereof.

In another embodiment of the invention, a treating step is included after the fragmentation and labeling steps to decrease or eliminate unreacted labeling agent. This step limits or eliminates non-specific signals that otherwise result from the presence of the unreacted label. Such a treating step may involve adding a quencher compound to the labeling reaction, or may involve physically separating the labeled nucleic acid fragments from unreacted labeling agents using any of a variety of methods.

A quencher is a compound that (1) forms soluble complexes with the metal cations in the reaction mixture, (2) precipitates the metal cations from the reaction mixture or (3) reacts with the residual labeling agent, thus, effectively removing it from the mixture. Soluble complexes can be formed, for example by using a chelating agent such as EDTA. Precipitable complexes can be formed by adding pyrophosphate anions Quencher compounds can readily be selected by one skilled in the art based on standard chemical interactions with the particular reactive groups involved in the labeling reaction. Preferred quenchers include pyrophosphate or thiol derivatives such as dithiothreitol, cysteine, gluthatione, mercaptosuccinic acid. Alternatively, or in addition to using a quencher, the treating step may remove unreacted label by methods that physically separate the labeled nucleic acid from the unattached labeling agent. Separating the unattached label from the labeled nucleic acid fragments may involve extracting the unreacted label into at least one organic solvent, such as 1-butanol, 2-butanol, isopentyl alcohol, 1-pentanol or cyclohexanol. A preferred solvent is 1-butanol. Another preferred extraction method includes acidifying the labeleing mixture before the solvent extraction. Alternatively, the organic solvent used for extraction is mixed with ethylene-diamine-tetraacetic acid (EDTA) before the extraction process begins.

Accordingly to another embodiment, the treating step is not carried out by the precipitation of nucleic acid fragments in a mixture of sodium acetate and cold isopropanol.

Purification of labeled nucleic acid fragments may also be effected by removing the unattached label using a solid phase extraction method. The solid phase support for such an extraction method is preferably beads, gel-filtration resins (e.g., Sephadex™, Sephacryl™ and BioGel™), gels or membranes (e.g., nylon, nitrocellulose, glass fiber or silica). Particularly preferred solid phase extraction media include gel-filtration resin Sephadex™ G-50, silica membranes and silica beads. The solid phase extraction methods are preferably performed using a column to contain the solid phase support and the solutions can be moved through the column using gravity-flow, vacuum suction, or positive pressure such as by centrifugation or used of a syringe attached to the top of the column. Before applying the labeling reaction mixture to a solid phase medium for extraction, a chelating agent such as EDTA is added to the mixture. In one preferred embodiment, the solid phase is paramagnetic particles coated with silica and the captured labeled nucleic acid fragments are eluted with betaine.

Solid phase purification methods are fast, simple, efficient and does not use organic solvents. Furthermore, due to its binding capacity limit, the solid support can be adapted to remove excess labeled fragments that may cause signal saturation during the detection step.

Additional or alternative methods for treating the labeling mixture to decrease the amount of unreacted labeling agent include precipitating the fragmented nucleic acids in a saline buffer containing betaine, a trialkyl ammonium salt derivative such as DTAB (dodecyl trimethylammonium bromide) or CTAB (cetyl trimethylammonium bromide) and exogeneous DNA. The labeling mixture can also be diluted to lower the concentration of unreacted labeling agent before the detecting step.

Although not wishing to be bound to any particular mechanism, the present methods of fragmenting and labeling nucleic acids may attach the label to a phosphate group or thiophosphate group in the nucleic acid. Such attachment may occur at a terminal or internal phosphate or thiophosphate group in the polymer These methods are illustrated by the examples that follow that demonstrate some preferred embodiments of the present invention.

EXAMPLE 1

Preparation of RNA Amplicons

To produce nucleic acids for fragmentation and labeling the following nucleic acid amplification reactions were performed. These reactions used two different sources of nucleic acid as the target, one derived from *Mycobacterium tuberculosis* and the other derived from the human immunodeficiency virus, HIV-1.

*Mycobacterium* 16S Amplicons

Amplicons of 16S rRNA of *Mycobacterium tuberculosis* were obtained using transcription mediated amplification (TMA) (Kacian et al., U.S. Pat. Nos. 5,399,491 and 5,554, 516; Kacian et al., PCT Patent App. No. WO 93/22461; McDonough et al., PCT Pat. App. No. WO 94/03472; and Ryder et al., PCT Pat. App. No. WO 95/03430). Amplification reactions were carried out using $10^6$ copies of rRNA target (*M. tuberculosis* 16S) and the reagents and methods of the *Mycobacterium Tuberculosis* Direct (ID) kit (Gen-Probe Incorporated, San Diego, Calif., USA). Primers used in TMA are disclosed in an application entitled "Methods and Compositions for Detecting *Mycobacterium* Species Using Nucleic Acid Amplification" which is being filed separately by the applicants on the day previous to the fling date of this application.

Briefly, after mixing the target nucleic acid, the primers and the amplification substrates, the amplification mixture was incubated at 42° C. for 1 hr. TMA product was analyzed by electrophoresis on a 6% polyacrylamide gel containing 7M urea and the separated amplicon products were visualized after ethidium bromide staining, to assess the product size and quantity by comparison with an RNA standard on the gel.

HIV-1 Amplicons

HIV amplicons were prepared using a polymerase chain reaction, as described by Kozal et al. (1996, Nature Med. 2 (7); 753–759). Briefly, DNA was extracted from $10^6$ cocultured cells by first treating the cells with lysis buffer (10 mM Tris-HCl, pH 8.3, 2.5 mM $MgCl_2$, 0.45% Tween™-20, 50 mM KCl, 0.1 mg/ml proteinase K) for 2 hr at 56° C.

A set of nested PCR reactions were used to amplify the HIV 1 DNA. The first reaction generated a 1200-bp amplicon using around 1.0 µg of input DNA and the two following primers:

aattaaccctcactaaagggagaCA-GAGCCAACAGCCCCACCA (SEQ ID NO:1, in which a T3 RNA polymerase promoter sequence is shown in lowercase), and taatacgactcactatagggagaTTTC-CCCACTAACTTCTGTATGTCATTGACA (SEQ ID NO:2, in which a T7 RNA polymerase promoter sequence is shown in lowercase). The PCR reaction was carried out in a reaction mixture containing 100 mM Tris-HCl, pH 8.3, 500 mM KCl, 1.5 mM $MgCl_2$, 0.2 µM each dNTPs, 0.2 FM primers (each) and 1.25 units Taq DNA polymerase. The reaction was incubated at 94° C. for 30 s, 55° C. for 30 s, 72° C. for 2 min for 25 cycles and 72° C. for 10 min for the last cycle.

The second reaction produced a 460-bp sequence, internal to the first amplified sequence, by using the SEQ ID NO: 1 primer as used in the first PCR and a third primer having the sequence taatacgactcactatagggagaGGGCCA TCCATTC-CTGGCTTTAATTT (SEQ ID NO: 3). The reaction was incubated at 94° C. for 30 s, 63° C. for 30 s, 72° C. for 1 min for 30 cycles, and 72° C. for 10 min for the last cycle. The PCR products were transcribed by using 20 U of T3 or T7 RNA polymerase in an in vitro reaction containing 40 mM Tris $Ac_2$, pH 8.1, 100 mM KAc, 30 mM $MgAc_2$, 10 mM DTT and 1.25 mM rNTPs.

The product size and quantity was assessed on a gel as described above.

For labeling reactions, RNA amplicons were used without further purification.

EXAMPLE 2

Background Reduction by Using Extraction with Organic Solvents

Imidazole and $MnCl_2$ were obtained from Sigma-Aldrich Chimie (St Quentin Fallavier, France) and 5-(bromomethyl)fluorescein was purchased from Molecular Probes (Eugene, Oreg., USA, reference B1355).

Amplicons of 16S rRNA were prepared as described in Example 1. Each labeling reaction (100 µl) included. RNA molecules (5 µl of TMA reaction mixture), 6 µl imidazole (0.1 M), 6 µl of $MnCl_2$ (1 M) 2 µl of 5-(bromomethyl)fluorescein (50 mM dissolved in DMF) and 81 µl of pure water. The reactions were mixed and incubated at 65° C. for 30 min.

Product was hybridized, detected and analyzed on an immobilized probe array on a DNA chip (GENECHIP®) using the manufacturer's protocol (Affymetrix, Santa Clara, Calif., USA). This DNA chip is designed for the detection and 4-L tiling of 16S rRNA of *M. tuberculosis* (region 213–415 of M20940 sequence <<Genbank>>, as described in Troesch et al., 1999, J. Clin. Microbiol. 37(1): 49–55). The results, obtained using functions available on GENE-CHIP® software (Affymetrix), included the following: BC: nucleotide base call (expressed in percentage); S: mean signal intensities for probe array cells (expressed in relative fluorescence unit : RFU); B : mean background intensities (expressed in RFU); and S/B ratio of signal to background. For this assay, 96.2% base calling was achieved with a mean signal of 5488 RFU and a background of 2420 RFU, to give a S/B ratio of 2.3.

This result shows that useful base calling and signal intensity can be obtained by using only 5% of amplicons generated in a single amplification region The S/B ratio, however, was relatively low.

In other experiments, smaller volumes of fragmentation and labeling mixtures were tested. In these experiments, the 16S rRNA amplicons were prepared as described in Example 1 using TMA amplification. Labeling reactions of 25 µl and 50 µl were then prepared. The 25 µl-reactions contained: RNA molecules (5;1 of TMA reaction mixture), 1.5 µl imidazole (0.1 M), 1.5 µl $MnCl_2$ (1 M), 2 µl 5-(bromomethyl)fluorescein (50 mM in DMF) and 15 µl of pure water. The 50 µl-reactions contained: RNA molecules (5 µl of TMA reaction mixture), 3 µl imidazole (0.1 M), 3 µl $MnCl_2$ (1 M), 2 µl 5-(bromomethyl)fluorescein (50 mM in DMF) and 37 µl of pure water. Both volumes were mixed and incubated at 65° C. for 30 min.

After incubation, pure water was added to each mixture to bring the final volume to 100 µl. Then, the labeling reaction products was hybridized, detected and analyzed on a DNA-chip using the manufacturer's protocol (GENECHIP®, Affymetrix, Santa Clara, Calif., USA), using the 4-L tiling DNA chip as described above.

The results are shown below.

| Labeling volume | BC % | S | B | S/B |
| --- | --- | --- | --- | --- |
| 25 µl | 98.4 | 4532 | 2363 | 1.9 |
| 50 µl | 98.4 | 5682 | 2462 | 2.3 |

These results show that labeling reactions can be performed in smaller volumes without affecting base calling or intensity levels.

To increase the S/B ratio, a purification step was included after the fragmentation and labeling reaction was completed. Here, organic solvents in a washing buffer were used to reduce the amount of unattached labeling agent in the mixture that was applied to the DNA chip for detection of the labeled RNA fragments.

Amplicons of 16S rRNA of *M. tuberculosis* were prepared as described in Example 1. Fragmentation and labeling of the amplicons were performed in 25 µl reactions as described above. After fragmentation and labeling, pure water was added to obtain a final volume of 100 µl. Then, the reaction product was hybridized, detected and analyzed on a DNA chip as described above, except that the washing buffers contained either 5% (v/v) of N,N-dimethylformamide (DMF) or 5% (v/v) of dimethyl sulfoxide (DMSO).

These results are shown below.

| Assay | Description | BC % | S | B | S/B |
|---|---|---|---|---|---|
| 1 | Wash buffer without solvent | 96.8 | 13263 | 8420 | 1.6 |
| 2 | Wash buffer with 5% DMF | 98.4 | 5748 | 1399 | 4.1 |
| 3 | Wash buffer with 5% DMSO | 97.3 | 5900 | 1655 | 3.6 |

The results show that the addition of organic solvents in washing buffers reduces the background levels, probably by increasing the solubility of unattached 5-(bromomethyl) fluorescein label in the washing buffer, thereby efficiently removing it from the DNA chip. The base call percentage was also higher in assays that included DMSO or DMF in the washing buffers.

As another method for improving detection on a DNA chip, an extraction of the fragmentation and labeling reaction mixture with an organic solvent was included before the hybridization step. The fragmentation and labeling reaction mixture contained: 16S rRNA amplicons (50 µl of TMA), 15 µl imidazole (0.1 M), 15 µl MnCl$_2$ (1 M), 5 µl 5-(bromomethyl)fluorescein (50 mM in DMSO) and pure water added for a final volume of 250 µl. The reaction mixture was mixed and incubated at 65° C. for 30 min.

Then, 100 µl of the reaction mixture was extracted by using 900 µl of water-saturated 1-butanol. After 1-butanol addition, the solution was vigorously vortex mixed and centrifuged to separate the aqueous and organic phases. 100 µl of the aqueous phase was mixed with 700 µl hybridization buffer (5X SSPE, 3 M betaine, 5 mM DTAB, 250 µg/ml salmon DNA) and hybridization on the DNA chip was performed as described above. Using this procedure, the BC was 98.4%, the signal was 2131 RFU and the background was 314 RFU, resulting in a S/B ratio of 6.8. These results show that the background level was reduced by use of an organic solvent extraction after the fragmentation and labeling reaction, without loss of base call percentage.

To determine if larger volume reactions could similarly be used, an entire 100 µl TMA reaction volume was used. In this case, labeling reagents were added directly in TMA reaction tube as follows. To the TMA reaction (100 µl) were added: 15 µl imidazole (0.1 M), 15 µl MnCl$_2$ (1 M), 5 µl 5-(bromomethyl)fluorescein (50 mM in DMF) and pure water to a final volume of 250 µl. The reaction medium was mixed and incubated at 65° C. for 30 min.

Alternatively, the same protocol was performed, followed by a 1-butanol purification performed substantially as describe above. Then, for both procedures (i.e., with and without organic solvent extraction), 100 µl of the reaction product was hybridized, detected and analyzed on a DNA chip as described above. These results are shown below.

| Description | BC % | S | B | S/B |
|---|---|---|---|---|
| 100 µl volume, without extraction | 97.8 | 1631 | 723 | 2.2 |
| 100 µl volume, with extraction | 98.4 | 3634 | 753 | 4.8 |

This protocol allowed fragmentation and labeling of the amplicons without an additional transfer step of amplicons to another tube because the labeling reagents were added to the TMA tube following amplification.

Similar assays were performed using HIV-1 amplicons produced as described in Example 1. These fragmentation and labeling reactions (250 µl) contained: HIV-1 protease RNA amplicons (50 µl), 15 µl imidazole (0.1 M), 15 µl MnCl$_2$ (1 M, 5 µl 5bromomethyl)fluorescein (100 mM in DMSO) and 165 µl of pure water; and were mixed and incubated at 60° C. for 30 min. For organic solvent extractions, two extractions using 1-butanol were performed As described above using 250, 300, 400 or 1000 µl butanol per extraction. Then the reaction product was hybridized, detected and analyzed on a DNA chip as described above, using a DNA chip for detection of the HIV-1 protease gene (Kozal et al., 1996, Nature Med. 2(7): 753–758). The results, shown below, indicate that two organic solvent extractions substantially decreased background for all of the volumes used.

| Extraction volume | BC % | S | B | S/B |
|---|---|---|---|---|
| 2 × 250 µl | 98.2 | 900 | 274 | 4.3 |
| 2 × 300 µl | 95.3 | 1103 | 214 | 6.2 |
| 2 × 400 µl | 96.6 | 1583 | 271 | 6.8 |
| 2 × 1000 µl | 96.6 | 1003 | 216 | 5.6 |

The protocol was modified by adding EDTA (10 mM) to the fragmentation and labeling reaction mixture before the 1-butanol extraction step. This addition increased solubility of the labeled RNA fragments and prevented precipitation caused by Mn$^{2+}$ metal ions. As shown below, addition of EDTA improved the detection step both for BC and increasing the S/B ratio.

| Description | BC % | S | B | S/B |
|---|---|---|---|---|
| 1-butanol extraction | 96.2 | 1160 | 251 | 4.6 |
| 1-butanol + EDTA extraction | 98.4 | 1303 | 228 | 5.7 |

In addition to 1-butanol, other organic solvents were also tested using similar extraction procedures, with 16S rRNA amplicons as the target nucleic acid for fragmentation and labeling. The results for each solvent are shown below, showing that a variety of organic solvents can be used to effectively remove unattached labeling agent.

| Extraction solvent | BC % | S | B | S/B |
|---|---|---|---|---|
| 1-Butanol | 94.1 | 5387 | 357 | 15.1 |
| 2-Butanol | 97.3 | 3289 | 291 | 11.3 |
| Isopentyl Alcohol | 94.6 | 4505 | 488 | 9.2 |
| Cyclohexanol | 94.6 | 4079 | 248 | 16.4 |
| 1-Pentanol | 93.0 | 4166 | 398 | 10.5 |
| 1-Butanol/Nitromethane | 93.0 | 4799 | 309 | 15.5 |

As an alternative to organic solvent extraction of the unattached label, precipitation of the fragmented and labeled nucleic acid fragments was also tested. In this experiment, HIV-1 amplicons were prepared as described in Example 1. Each reaction included: RNA amplicons (50 µl), 6 µl imidazole (0.1 M), 6 µl MnCl$_2$ (1 M), 2 µl 5-(bromomethyl) fluorescein (50 mM in DMSO) and pure water to a final volume of 100 µl the mixed solution was incubated at 65° C. for 30 min. For control reactions in which the fragmented RNA was not precipitated, the hybridization and detection steps were performed as described above using the HIV-1 specific DNA chip. For experimental reactions that included a precipitation step, the precipitation step was performed prior to hybridization on the chip. For precipitation, the reaction mixture was mixed wit 700 μl of hybridization buffer (5X SSPE, 3 M betaine, 5 mM DTAB, 25 μg/ml salmon sperm DNA) at room temperature by vortexing. The precipitate was pelleted and the supernatant was removed. The pellet was resuspended in 500 μl of the hybridization buffer and hybridization, detection and analysis were performed on the HIV-1 specific DNA chip as described above.

The results are shown below for both procedures.

| Description | BC % | S | B | S/B |
|---|---|---|---|---|
| No Precipitation | 94.6 | 2008 | 1297 | 1.5 |
| Precipitation | 96.6 | 2315 | 483 | 4.8 |

Without precipitation, the signal intensity was high but the S/B ratio was low (1.5); with precipitation, the background decreased and the S/B ratio increased.

EXAMPLE 3

Solid Phase Extraction of Unattached Label

In this example, labeled fragments, following fragmentation and labeling of nucleic acids, were physically separated from unattached label using solid phase extraction.

Silica Beads Solid Support

The solid phase reagent used was magnetic silica beads. The target nucleic acid was 16S rRNA amplicons, prepared as described in Example 1. The reaction included: 50 μl of TMA reaction mixture, 9 μl imidazole (0.1 M), 9 μl MnCl$_2$ (1 M), and 3 μl 5-(bromomethyl)fluorescein (100 mM in DMSO) which were mixed and incubated at 60° C. for 30 min.

The solid phase extraction was performed using commercially available reagents, the Wizard PureFaction™ Plasmid DNA Purification System Starter Pack Promega, Madison, Wis., USA). In this procedure, the fragmentation and labeling reaction was mixed with 25 μl of MagneSil Paramagnetic Particles and 1 ml of 4/40 Wash solution, agitated vigorously (by vortex), and then the tube was placed on a magnet support to hold the magnetic beads to the side of the tube. The beads were washed using 1 ml of 80% ethanol and the labeled RNA fragments were eluted by using 100 μl of 10 mM Tris-Cl, pH 8.5. The eluate was hybridized, detected and analyzed on a DNA chip as described above. The results of this purification procedure, compared to those obtained using 1-butanol extraction are shown below.

| Purification | BC % | S | B | S/B |
|---|---|---|---|---|
| 1-butanol extraction | 99.5 | 1639 | 536 | 3.1 |
| Silica beads purification Assay 1 | 98.4 | 875 | 133 | 6.6 |
| Silica beads purification Assay 2 | 97.8 | 773 | 135 | 5.7 |

These results show that solid phase extraction using silica beads reduces background and increases the S/B value.

In a separate experiment, a similar silica bead solid phase extraction was performed but the elution was performed using betaine (5 M dissolved in hybridization buffer, 300 μl) Hybridization was then performed on a DNA chip as described above, using hybridization buffer without betaine. When the labeled fragments eluted with betaine were hybridized, the BC was 99.5%, the signal was 2424 RFU, the background was 170 RFU and the S/B was 14.3.

Silica Membrane Solid Support

In a separate experiment, a silica membrane was used in place of the magnetic silica beads for post-labeling purification. In this experiment, the fragmentation and labeling reaction was performed using 16S rRNA amplicons in a 100 μl volume reaction as described in Example 2, and the post-labeling purification was performed using a silica membrane (QIAQUICK™ Nucleotide Removal kit, Qiagen, Hilden, Germany). For purification, 0, 15 or 75 μl of 0.5 M EDTA and 685 μl of PN Buffer were added to the reaction mixture and the solution was vortexed vigorously. Sample was then processed following the manufacturer's protocol. The eluate was hybridized, detected and analyzed on a DNA chip as described above.

The results of this purification method, compared to those obtained using a 1-butanol extractions are shown below, showing that the silica membrane purification is comparable to extraction of unattached label using an organic solvent if EDTA was included in the mixture purified by the silica membrane method.

| Purification | EDTA (mM) | BC % | S | B | S/B |
|---|---|---|---|---|---|
| 1-butanol extraction | — | 94.6 | 7390 | 294 | 251 |
| QIAQUICK™ purification | 0 | 88.1 | 391 | 225 | 1.7 |
| | 15 | 95.7 | 8498 | 329 | 25.8 |
| | 75 | 98.4 | 6754 | 246 | 27.5 |

Similar silica membrane purification methods were used in a separate experiment but betaine (5 M) elution from the silica membrane was used to recover the labeled RNA fragments, substantially as described above. In this assay, the BC was 94.6%, the signal was 15836 RFU, the background was 502 RFU and the S/B ratio was 31.5.

QIAVAC™ Column Solid Support

An additional purification method was performed using a PCR purification kit with PN buffer and a vacuum system (QIAVAC™ 6S system) to draw materials through the column (Qiagen, Hilden, Germany). In this assay, 16S rRNA amplicons were fragmented and labeled as described in Example 2, and then 15 μl of 0.5 M EDTA and 685 μl of PN Buffer were added to the reaction mixture, the solution was vortexed vigorously and processed following the manufacturer's protocol. The column was washed with 1 ml of PE buffer and labeled nucleic acid fragments were eluted, hybridized, detected and analyzed on a DNA chip as described above.

The QIAVAC™ purification method produced 100% base cell, signal of 15,984 RFU, background of 390 RFU and a S/B ratio of 41. In comparison, similarly cleaved and labeled fragments that were purified using 1-butanol extraction produced 94.6% base call, signal of 7390 RFU, background of 294 RFU and a S/B ratio of 25.1.

Gel Filtration Solid Supports

Additional solid phase extraction protocols used gel filtration resins in small spin column format (SEPHADEX™, SEPHACRYL™ and BIOGEL™ resins were tested). These resins allow larger molecules (i.e., the labeled nucleic acid fragments) to be selectively eluted, while retaining the smaller molecules (unreacted labeling agent and other mixture components). The nucleic acid used for testing in these assays was 16S rRNA amplicons prepared substantially as described in Example 1, which was then subjected to fragmentation and labeling substantially as described in Example 2. The general procedure was to equilibrate a commercially available spin column containing a gel filtration resin (e.g., a SEPHADEX™ G-50 spin column from Pharmacia) with a 400 µl volume of a buffer (e.g., Tris-azide buffer, pH 7.4) by applying the buffer and then eluting it by centrifugation (1000×g for 1 min), repeating the procedure, and finally wetting the resin with an additional 400 µl of the same buffer. Then a 100 µl reaction mixture was applied to the prepared column and the labeled nucleic acid fragments were eluted by centrifuging the column at 1000×g for 1 min.

To obtain efficient recovery of labeled nucleic acid fragments from a labeling reaction mixture, EDTA (25 mM to 125 mM was added and mixed with the labeling reaction mixture before it was applied to the gel filtration resin for purification. Optimal recovery and detection (on a DNA chip, assessed by the S/B ratio) was observed when the EDTA concentration was 25 mM or 50 mM; at EDTA concentrations of 75 mM and higher, the background on the detection chip was increased. Typically, 50 mM EDTA was added to the labeling mixture before it was applied to the gel filtration resin.

The efficiency of this purification procedure was demonstrated using this basic procedure to purify labeled fragments obtained from 16S rRNA amplicons as described above. The purified labeled fragments ("purified+EDTA") were then detected after applying them to *Mycobacterium*-specific GENECHIP® substantially as described in Example 2 For comparison, the same type of labeled fragments obtained directly from a fragmentation and labeling reaction, without gel filtration purification ("unpurified"), was also applied and analyzed using the same DNA chip procedure.

Also, for comparison, the assay was done using the same type of labeled fragments that were purified by gel filtration but without adding EDTA ("purified—EDTA") to the labeling mixture before applying it to the column. These DNA chip analysis results are shown below.

| Sample | % BC | Signal (mean) | Background | S/B Ratio |
| --- | --- | --- | --- | --- |
| Unpurified | 89.2 | 13396 | 10334 | 1.3 |
| Purified – EDTA | 77.3 | 625 | 483 | 1.24 |
| Purified + EDTA | 95.7 | 3820 | 1185 | 3.03 |

These results show that gel filtration purification, in the presence of 50 mM EDTA, is a quick and effective method of providing labeled nucleic acid fragments that can be readily detected on a DNA probe array.

EXAMPLE 4

Effect of 5-(bromomethyl)fluorescein Concentration on Labeling

In this example, differing amounts of labeling agent were used in the fragmentation and labeling reaction to determine if the labeling agent concentration affected the assay. Amplicons of 16S rRNA were prepared as described in Example 1. The reactions each included: RNA (50 µl of TMA), 9 µl imidazole (0.1 M), 9 µl $MnCl_2$ (1 M), varying amounts of 5-(bromomethyl)fluorescein (50 mM in DMF) to achieve final concentrations of 1 mM (3 µl), 2 mM (6 µl) or 4 mM (12 µl) and pure water to achieve a final volume of 150 µl. The mixture was mixed and incubated at 60° C. for 30 min. Then the labeling reaction mixture was purified using 1-butanol extraction as described above and 100 µl of the purified product was hybridized, detected and analyzed on a DNA chip as described in Example 2. The results are reported below, showing that all of the tested concentrations of labeling agent efficiently labeled the fragmented RNA Higher signal was produced for the higher concentrations of labeling agent, without a significant increase in the background level.

| [5-(bromomethyl)fluorescein] | BC % | S | B | S/B |
| --- | --- | --- | --- | --- |
| 1 mM | 96.8 | 2178 | 311 | 7.0 |
| 2 mM | 96.8 | 3511 | 556 | 6.3 |
| 4 mM | 94.6 | 3836 | 421 | 9.1 |

EXAMPLE 5

Effect of pH on Fragmentation and Labeling Reactions

In these experiments, the pH of the imidazole reagent was adjusted to 6, 6.8 and 7.0 for use in the fragmentation and labeling reactions which contained: 16S rRNA amplicons (50 µl of TMA reaction), 45 µl of a pH-adjusted mixture of imidazole (20 mM) and $MnCl_2$ (200 mM); 5 µl 5-(bromomethyl)fluorescein (100 mM in DMSO) and pure water to a final volume of 150 µl. The reactions were mixed and incubated at 60° C. for 30 min. Then, hybridization, detection and analysis were performed on a DNA chip as described in Example 2. The results for the different pH conditions of the reactions are shown below. Based on these results, all of the pH conditions tested produced detectably labeled fragments that provided base calling of 98% or more; pH 7.0 appears to be optimal.

| Reaction pH | BC % | S | B | S/B |
| --- | --- | --- | --- | --- |
| 6.0 | 98.9 | 2948 | 202 | 14.6 |
| 6.8 | 98.4 | 4052 | 210 | 19.3 |
| 7.0 | 100 | 4668 | 234 | 19.9 |

EXAMPLE 6

Influence of Multivalent Metal Cations and Labeling Agents on DNA Labeling

This example shows the relative efficiencies of fluorescein labeling of different single-stranded oligonucleotides, using different labeling agents and multivalent metal cations in the fragmentation and labeling reactions. Labeling of DNA, DNA containing an internal thiophosphate nucleotide and DNA having a 3'-thiophosphate with 5-(bromomethyl) fluorescein and 6-iodoacetamidofluorescein were compared in the presence or absence of different metal cations.

The oligonucleotides used in the fragmentation and labeling experiments were the following:

GCTCGTTGCGGGACTTAACCCAACAT (SEQ ID NO:4);

GCTCGTTGCGGGACTT-s-AACCCAACAT (SEQ ID NO:5) where <<-s->> indicates a thiophosphate between nucleotides at positions 16 and 17; and GCTCGTTGCGGGACTTAACCCAACAT-s (SEQ ID NO:6) where <<-s->> indicates a 3' terminal thiophosphate.

The buffer for the reaction was Tris-HCl buffer, pH 8.1, and the different multivalent metal cations were: $Zn^{2+}$, $Mn^{2+}$, $Co^{2+}$, $Ni^{2+}$, $Cd^{2+}$, $Pb^{2+}$, $Ce^{3+}$, $Tb^{3+}$, $Yb^{3+}$, $Cr^{3+}$, $In^{3+}$, $Be^{2+}$, $Sn^{2+}$, $Rb^{+}$, and $Cs^{+}$ (all in solution with $Cl^{-}$ counterions). The negative control containing no multivalent cations was an equivalent volume of pure water. The labeling agents, dissolved in dry N, N-dimethylformamide (DMF), were: 5-(bromomethyl)fluorescein and 6-iodoacetamidofluorescein (Molecular Probes, Inc., Eugene, Oreg. USA). The DMF-dissolved compounds were generally added to reaction mixtures such that the final concentration of DMF in the mixture was 5% (v/v).

The typical fragmentation and labeling reaction (100 $\mu$l) contained (with final concentrations indicated in parentheses for each component): 30 $\mu$l of oligonucleotide (6.667 OD/ml; 0.2 OD=0.00932 mM), 50 $\mu$l of 100 mM Tris-HCl buffer (50 mM), 10 $\mu$l of 10 mM metal cation (1 mM) or pure $H_2O$, and 10 $\mu$l of 2.5 mM labeling reagent in DMF (0.25 mM). The reaction mixture was mixed by vortexing and incubated at 60° C. for 30 min. The labeled products are purified by adding to the labeling reaction mixture 10 $\mu$l of 3 M sodium acetate, pH 5.0, then 150 $\mu$l water-saturated 1-butanol, and mixing by vortexing. After the phases separated, the aqueous phase (113 $\mu$l) was removed to a clean tube to which was added 400 $\mu$l ethanol and the solution was vortexed and incubated on dry ice for 15 min. The mixture was centrifuged 15 min at 14,000 rpm, the supernatant removed and the pellet was washed with 100 $\mu$l of cold 70% ethanol. The pellet was resuspend in 500 $\mu$l of 100 mM sodium carbonate buffer, pH 9.5. The products (labeled DNA and unlabeled DNA) were measured using UV spectroscopy or reverse phase HPLC and peak integration.

The results of these experiments are summarized in Table 1 for labeling of oligonucleotides of SEQ ID NO:5 and SEQ ID NO:6 with 5-(bromomethyl)fluorescein ("5-BMF") and 6-iodoacetamidofluorescein ("6-IA-F") in the presence of 15 multivalent metal cations.

TABLE 1

Percent fluorescein incorporation (labeling yield).

| Metal Cation | SEQ ID NO: 5 | | SEQ ID NO: 6 | |
| --- | --- | --- | --- | --- |
|  | 5-BMF | 6-IA-F | 5-BMF | 6-IA-F |
| None ($H_2O$) | 0.933 | 3.10 | 20.8 | 58.6 |
| $Yb^{3+}$ | 78.7 | 48.4 | 98.6 | 60.9 |
| $Ce^{3+}$ | 62.9 | 46.7 | 69.4 | 56.5 |
| $Tb^{3+}$ | 51.8 | 45.4 | 66.9 | 64.2 |
| $In^{3+}$ | 44.8 | 32.7 | 42.8 | 34.1 |
| $Pb^{2+}$ | 43.6 | 54.5 | 59.8 | 69.0 |
| $Cr^{3+}$ | 24.5 | 29.8 | 33.7 | 62.3 |
| $Zn^{2+}$ | 21.1 | 20.5 | 13.6 | 36.0 |
| $Be^{2+}$ | 12.6 | 10.4 | 13.5 | 27.0 |
| $Cd^{2+}$ | 4.38 | 4.70 | 5.72 | 22.3 |
| $Co^{2+}$ | 3.94 | 5.52 | 17.2 | 61.2 |
| $Sn^{2+}$ | 3.59 | 4.13 | 23.1 | 50.2 |
| $Mn^{2+}$ | 2.70 | 2.50 | 28.4 | 63.7 |
| $Ni^{2+}$ | 1.70 | 2.22 | 19.5 | 67.0 |
| $Cs^{+}$ | 1.17 | 1.12 | 22.0 | 58.7 |
| $Rb^{+}$ | 1.04 | 1.09 | 20.4 | 57.8 |

Labeling of the DNA containing an internal thiophosphate (SEQ ID NO:5), using either 5-BMF or 6-IA-F, was enhanced, relative to the negative control, by the presence of trivalent metal ions and divalent $Pb^{2+}$, $Zn^{2+}$, and Be but not by the other metal cations tested. There is little difference between the two labeling agents when a common metal cation was used. Labeling of the nucleic acid with a 3'-thiophosphate (SEQ ID NO:6) by 5-BMF was enhanced relative to the negative control by the presence of $Pb^{2+}$ and the trivalent metal cations tested, but not by the other cations tested. Labeling of the nucleic acid with a 3'-thiophosphate (SEQ ID NO:6) by 6-IA-F was enhanced relative to the negative control primarily by $Pb^{2+}$ and $Ni^{2+}$. Labeling by 6-IA-F of SEQ ID NO:6 was relatively high in the negative control without metal cations.

The labeling yield obtained with the oligonucleotide that contains no thiophosphate group (SEQ ID NO:4) was below 10% for all of the metal cations tested. The thiophosphate-free DNA was not detectably labeled in the absence of metal cations (i.e., the water control).

EXAMPLE 7

Influence of Metal Cations and Labeling Agents on RNA-α-s Labeling

This example shows the relative attachment of fluorescein onto thiophosphate-containing RNA (RNA-α-S), using different labeling agents and metal cations. Fluorescein labeling of RNA containing internal or 3'-terminal thiophosphates was compared using two labeling agents, 6-IA-P and 5-iodoacetamidofluorescein (5-IA-F), in the presence or absence of different metal cations.

The protocol for the experiment is similar to the protocol described in Example 6 but the oligonucleotides used were RNA polymers having the following sequences:

GCUCGUUGCGGGACUU-s-AACCCAACAU (SEQ ID NO:7), where "-s-" indicates a thiophosphate between the two nucleotides at positions 16 and 17, and GCUCGUUGCGGGACUUAACCCAACAU-s (SEQ ID NO:8), where "-s-" indicates a 3' terminal thiophosphate.

In these labeling reactions the metal cations tested were $Mg^{2+}$, $Cr^{3+}$, $Mn^{2+}$, $Ni^{2+}$, $Zn^{2+}$, $In^{3+}$, $Pb^{2+}$, $Ce^{3+}$, $Eu^{3+}$, $Tb^{3+}$ and $Yb^{3+}$ (all with Cl counterions); pure water was the negative control. The labeling agents, 5-IA-F and 6-IA-F, were each dissolved in dry DMF. The 100 $\mu$l reactions contained (with final concentrations indicated in parentheses): 50 $\mu$l of 100 mM Tris-Cl buffer, pH 8.1 (50 mM), 30 $\mu$l of 6.667 OD per ml oligomer (0.2 OD=0.00932 mM final), 10 $\mu$l of 10 mM metal cation (1 mM) or pure water, and 10 $\mu$l of 2.5 mM labeling reagent (0.25 mM); final DMF concentration was 5%. The combination was mixed by vortexing and incubated at 60° C. for 30 min.

After purification using 1-butanol extraction as described in Example 6, a 120 $\mu$l of aqueous phase was precipitated with ethanol and the pelleted nucleic acid was resuspended in 500 $\mu$l of 100 mM sodium carbonate buffer, pH 9.5. The labeling yield was analyzed by UV spectroscopy as described in Example 6. The results are summarized in Table 2, in which "ND" means not determined. Results for testing with $Mn^{2+}$, $Zn^{2+}$ and $In^{3+}$ are not included in the table because they exhibited relatively low activity.

TABLE 2

Percent fluorescein labeling using different labeling agents, metal cations and oligonucleotides.

| | SEQ ID NO: 7 | | SEQ ID NO: 8 | |
|---|---|---|---|---|
| Metal Cation | 5-IA-F | 6-IA-F | 5-IA-F | 6-IA-F |
| $Cr^{3+}$ | 11.3 | 23.0 | 19.2 | 31.2 |
| $Ce^{3+}$ | 28.1 | 19.2 | 30.2 | 20.1 |
| $Pb^{2+}$ | 26.5 | ND | 27.1 | 21.4 |
| $Yb^{3+}$ | 16.8 | 20.5 | 20.7 | 22.8 |
| $Tb^{3+}$ | 26.3 | 21.8 | 18.1 | 17.9 |
| $Eu^{3+}$ | 21.5 | 11.1 | 13.1 | 15.3 |
| $Ni^{2+}$ | 0 | 0 | 4.83 | 1.94 |
| $Mg^{2+}$ | 0 | 0 | 0.774 | 1.98 |
| $H_2O$ | 0 | 0.090 | 1.11 | 4.35 |

Labeling of RNA, like DNA, is metal cation and labeling agent sensitive Both 5-IA-F and 6-IA-F labeled RNA-α-S to similar extents, with the 3'-terminal RNA-α-S being labeled slightly better than the RNA containing an internal thiophosphate. Trivalent metal cations or $Pb^{2+}$ provided the most enhanced labeling relative to the negative control with both labeling agents

EXAMPLE 8

Efficiency of RNA Fragmentation by Metal Cations

This example shows the relative efficiencies of RNA fragmentation in the presence of various metal cations. The substrates for fragmentation in these experiments were synthetic RNA oligonucleotides having the following sequences:

GCUCGUUGCGGGACUUAACCCAACAU (SEQ ID NO:9), and

GCUCGUUGCGGGACUU-s-AACCCAACAU (SEQ ID NO:7), where <<-s->> indicates a thiophosphate between nucleotides 16 and 17.

Synthetic complimentary RNA sequences to SEQ ID NO:7 and SEQ ID NO:9 were made and used to form a double-stranded RNA with the appropriate complementary oligonucleotide. For fragmentation testing, both single-stranded and double-stranded RNA were used.

The probe used in the detection step was a 26-nucleotide sequence complimentary to SEQ ID NO:9, with an acridinium ester (AE) label between positions 16 and 17 (described in Nelson et al., 1996, Nucleic Acids Res. 24(24): 4998–5003) The general method involves fragmenting 100 fmoles of RNA in a total volume of 100 μl (i.e., the final RNA concentration in the reaction is 1 fmol/μl) in 50 mM imidazole buffer at pH 7.6, containing 2.5 μmoles of each of the metal cations tested. After the reaction incubated at 60° C. for 30 min, the fragmentation reaction was stopped by adding a 2- to 3-fold molar excess of EDTA, pH 8, relative to the metal cation concentration and incubating at −20° C. To monitor the amount of RNA fragmentation, about 5 fmol of RNA was taken from the mixture and probed with a 20-fold excess of the AE-labeled probe. All probe hybridizations were done at 60° C. for 60 min (in 1X PACE® 2 hybridization buffer, Gen-Probe, San Diego Calif., USA).

Probing a small amount of RNA from the fragmented material also allows the fragmentation mixture volume to be adequately diluted in the hybridization volume such that the fragmentation reaction components do not affect the hybridization of the probe to the target. About 200 μl of PACE® 2 selection reagent (Gen-Probe Incorporated, San Diego Calif., USA) was used to hydrolyze the unhybridized probe.

The hybridized probe was detected using a luminometer to detect chemiluminescence (as previously described by Nelson et al., supra). The chemiluminescence is expressed as relative light units or RLU.

For the double-stranded RNA, about 160 pmol of SEQ ID NO:9 was hybridized with 3-fold excess of the complimentary sequence in 1X PACE® 2 hybridization buffer at 65° C. for 30 min. The 3-fold excess complimentary strand concentration is used to ensure complete hybridization The AE-labeled probe has exactly the same sequence and, therefore, the excess strand will not bind to the probe.

A control reaction without metal cations (i.e., substituting pure water) was done in parallel, and the chemiluminescence signal of the control was used to calculate the percentage of fragmentation.

The metal cations chosen for fragmentation can be broadly divided into three different categories; (1) non-transition metals such as Mg, Sr, Ba (Group II), and Pb (Group IV); (2) transition metals, such as Zn, Cd, Mn, Fe, Co, Ni, and Ru, and (3) lanthanides, such as Ce, Eu, Tb, Tm, Yb, and Lu. The counterion for all the metal cations tested was Cl⁻ (all from Aldrich Chemical Co., Milwaukee, Wis., USA).

Table 3 shows the fragmentation efficiency of eighteen different multivalent metal cations at 0.25 mM on single- and double-stranded RNA in 50 mM imidazole buffer (pH 7.6), where the reaction was incubated at 60° C. for 30 min. All results are expressed as a percentage of fragmentation.

TABLE 3

Percent RNA fragmentation by metal cations.

| | Single stranded RNA | | Double stranded RNA | |
|---|---|---|---|---|
| Metal | SEQ ID NO: 9 | SEQ ID NO: 7 | SEQ ID NO: 9 | SEQ ID NO: 7 |
| $Mg^{2+}$ | 18 | 62 | 71 | 63 |
| $Sr^{2+}$ | 26 | 74 | 72 | 63 |
| $Ba^{2+}$ | 38 | <5 | 60 | 70 |
| $Pb^{2+}$ | 82 | 92 | 53 | 55 |
| $Zn^{2+}$ | 38 | 14 | 11 | 29 |
| $Cd^{2+}$ | 86 | <5 | 62 | 60 |
| $Mn^{2+}$ | 38 | 10 | 72 | 65 |
| $Fe^{2+}$ | 62 | 7 | <5 | <5 |
| $Co^{2+}$ | 33 | 47 | 72 | 69 |
| $Ni^{2+}$ | 69 | 58 | 68 | 52 |
| $Ru^{3+}$ | 95 | 95 | 72 | 60 |
| $Ce^{3+}$ | 58 | 58 | <5 | 27 |
| $Eu^{3+}$ | 52 | 35 | <5 | 16 |
| $Tb^{3+}$ | 40 | 52 | <5 | <5 |
| $Tm^{3+}$ | 43 | 57 | <5 | <5 |
| $Yb^{3+}$ | 45 | 54 | <5 | <5 |
| $Lu^{3+}$ | 48 | 52 | <5 | <5 |

All the lanthanides fragmented single-stranded RNA more efficiently than double-stranded RNA Among the transition metals, Zn and Fe fragmented double-stranded RNA less efficiently than single-stranded RNA. Most of the transition and the non-transition metals efficiently fragmented double-stranded RNA.

EXAMPLE 9

Efficiency of Fragmentation of Single-stranded RNA by Metal Cations in the Presence of Amplification Buffer This example shows that fragmentation of single-stranded RNA can also be accomplished in other buffer conditions, such as in the TMA solution conditions. The procedures used arc substantially the same as described in Example 8, with the following exceptions.

Negative TMA amplification reactions were performed as described in Example 1 in the absence of target RNA. The negative amplification reactions were pooled together to constitute a TMA solution. The synthetic RNA oligonucleotide (SEQ ID NO:7) was then spiked into this TMA solution for the fragmentation reactions. Four different fragmentation buffers were used, all at pH 7.5: imidazole, MOPS, HEPES, and PIPES (all from Aldrich Chemical Co, Milwaukee, Wis., USA). The buffers varied in concentrations from 50 mM to 200 mM with the TMA solution containing the synthetic RNA oligonucleotide diluted to a ratio of 1:20 or not diluted (ratio 1:1). Three different metal cations were tested ($Zn^{2+}$, $Ce^{3+}$ and $Tb^{3+}$), all at 5 mM The fragmentation yield was determined as described in Example 8 and the results summarized in Table 4 for the 1:20 dilution assays. Without dilution of the TMA solution, fragmentation was below 10%.

TABLE 4

Percent single-stranded RNA fragmentation by metal cations in amplification buffer.

| | Imidazole | | MOPS | | HEPES | PIPES |
|---|---|---|---|---|---|---|
| Metal | 50 mM | 200 mM | 50 mM | 200 mM | 50 mM | 50 mM |
| $Zn^{2+}$ | 3 | 22 | 20 | 25 | 22 | 22 |
| $Ce^{3+}$ | 62 | 75 | 68 | 69 | 75 | 79 |
| $Tb^{3+}$ | 50 | 70 | 57 | 60 | 71 | 61 |

These results show that fragmentation of RNA is also effective in a variety of buffering conditions in the presence of multivalent metal cations, particularly $Ce^{3+}$.

EXAMPLE 10

Fragmentation and Labeling of RNA and DNA-α-s As Detected by MALDI-TOF

This example shows fluorescein labeling of oligonucleotide fragments in the presence and absence of metal cations and whether fragmentation is associated with labeling. Fluorescein attachment to the oligonucleotides was quantified by absorption spectroscopy and compared to oligonucleotide fragments detected by MALDI-TOF (matrix-assisted laser desorption/ionization-time-of-flight) mass spectroscopy.

The fragmentation reactions were performed substantially as described in Example 6 using synthetic RNA and DNA oligonucleotides having the following sequences:

GCUCGUUGCGGGACUU (SEQ ID NO:10),

GCUCGUUGCGGGACUU-s (SEQ ID NO:11), which is identical to SEQ ID NO: 10 but includes a 3'-terminal thiophosphate, GCUCGUUGCGGGACUU-s-AACCCAACAU (SEQ ID NO:7), and GCTCGTTGCGGGACT T-s-AACCCAACAT (SEQ ID NO:5), where -s- indicates a thiophosphate between the bases 16 and 17.

In these assays, the buffer was imidazole, and the metal cations were $Zn^{2+}$ or $Tb^{3+}$ (both with $Cl^-$ counterions); pure water was the negative control. The labeling agents, in dry DMF, were 5-(bromomethyl)fluorescein or 6-iodoacetamidofluorescein. The 100 μl reactions contained (final concentrations shown in parentheses): 50 μl of 100 mM imidazole buffer, pH 7.6 (50 mM), 30 μl of 6.667 OD/ml oligomer (0.2 OD=0.00932 mM final), 10 μl of 25 mM metal cation (2.5 mM) or pure water, and 10 μl of 2.5 mM labeling reagent (0.25 mM), or pure water for the fragmentation-only reactions.

The reaction mixtures were mixed using vortexing and incubated at 60° C. for 30 min. After a purification step, 10 μl of sodium acetate (3 M, pH 5.0) and 150 μl of water-saturated 1-butanol were added and the mixture was mixed by vortexing, then incubated on dry ice for 15 min, centrifuged 15 min at 14,000 rpm, and the pellet was washed with 100 μl of cold 70% ethanol. The pellet was resuspended in 40 μl of pure water, and 3 μl were reserved for MALDI-TOF detection. The remaining portion was diluted to 500 μl with 100 mM sodium carbonate buffer, pH 9.5 for UV-Visible spectrophotometry.

For MALDI-TOF detection, a 3 μl sample of 5 OD/ml oligomer (0.015 OD) was mixed with 1 μl of 30 mM ammonium citrate buffer, pH 9.4, and 6 μl of 50 mg/ml 3-hydroxypicolinic acid (HPA, matrix) and a cation exchange resin by triturating about 10× with a pipeting device. The resin was allowed to settle, and a 2 μl sample was spotted onto a gold support, air dried for 20 min, and the mass data were collected using a PerSeptive Biosystems Voyager DE MALDI-TOP mass spectrometer. Masses were based on using the SEQ ID NO: 10 oligonucleotide as an external standard, MALDI-TOF labeling and fragmentation results of the reactions using 5-BMF and 6-IA-F, with or without the cations $Zn^{2+}$ or $Tb^{3+}$, are summarized in Tables 5 and 6. In Table 5, "−" indicates no fluorescein labeled oligomers detected, "+" indicates monofluorescein labeled oligomer detected, and "++" indicates difluorescein labeled oligomer detected. In Table 6, "−" indicates no fragmented products detected, "+" indicates a few fragmented products/groups (2–5) detected, "++" indicates more (8 −12) fragmented products detected, and "+++" indicates many fragmented products detected (>15). "ND" means not detected.

TABLE 5

Fluorescein Labeling of RNA and DNA oligonucleotides determined by MALDI-TOF mass spectrometry.

| Labeling Agent | Metal | SEQ ID NO:11 (RNA) | SEQ ID NO:10 (RNA) | SEQ ID NO:7 (RNA) | SEQ ID NO:5 (DNA) |
|---|---|---|---|---|---|
| 5-BMF | $Zn^{2+}$ | + | ++ | + | ++ |
| | $Tb^{3+}$ | − | ND | − | + |
| | None ($H_2O$) | − | − | − | − |
| 6-IA-F | $Zn^{2+}$ | − | − | + | ++ |
| | $Tb^{3+}$ | − | − | ND | − |
| | None ($H_2O$) | − | − | − | − |

TABLE 6

Fragmentation of RNA and DNA oligonucleotides determined by MALDI-TOF mass spectrometry.

| Labeling Agent | Metal | SEQ ID NO:11 (RNA) | SEQ ID NO:10 (RNA) | SEQ ID NO:7 (RNA) | SEQ ID NO:5 (DNA) |
|---|---|---|---|---|---|
| 5-BMF | $Zn^{2+}$ | ++ | +++ | ++ | − |
|  | $Tb^{3+}$ | ++ | ND | +++ | ++ |
|  | None ($H_2O$) | − | − | + | − |
| 6-IA-F | $Zn^{2+}$ | − | − | ++ | − |
|  | $Tb^{3+}$ | ++ | +++ | ND | ++ |
|  | None ($H_2O$) | − | − | + | − |
|  | $Zn^{2+}$ |  |  | + |  |
|  | None ($H_2O$) |  |  | + |  |

The quantitation of fluorescein labeling, detected by spectrophotometry, is shown in Table 7 as the percent of fluorescein attached to the oligonucleotide in the presence and absence of metal cations.

TABLE 7

Percentage of Fluorescein Attached

| Labeling Agent | Metal | SEQ ID NO:11 (RNA) | SEQ ID NO:10 (RNA) | SEQ ID NO:7 (RNA) | SEQ ID NO:5 (DNA) |
|---|---|---|---|---|---|
| 5-BMF | $Zn^2$ | 34.0 | 48.4 | 40.6 | 119 |
|  | $Tb^3$ | 23.2 | 23.9 | 15.3 | 31.1 |
|  | None ($H_2O$) | 5.21 | 0.511 | 5.05 | 0.683 |
| 6-IA-F | $Zn^2$ | 21.0 | 27.0 | 31.3 | 125 |
|  | $Tb^3$ | 8.17 | 6.32 | 4.82 | 16.0 |
|  | None ($H_2O$) | 3.88 | 0.579 | 0.939 | 1.63 |

These result show that both labeling agents, 5-BMF and 6-IA-P, were effective in labeling RNA oligonucleotide in the presence of $Zn^{2+}$ and $Tb^{3+}$; in the absence of metal cations there was little labeling by either labeling agent. Mass spectroscopy 15 detected singly and doubly fluorescein-labeled oligonucleotide only when the efficiency of labeling was greaser than 30% and 40%, respectively. Fluorescein labeling was efficient in the presence of $Zn^{2+}$ on all of the oligomers tested with 5-BMF and on the longer RNA and DNA oligomers with 6-IA-F. In the presence of $Zn^{2+}$ plus either alkylating agent, significantly more fragmentation occurred than in the absence of alkylating agent. $Tb^{3+}$ plus alkylating agents fragments DNA.

EXAMPLE 11

Fragmentation and Labeling of HIV-1 Amplicons Using CeCl₃ as the Metal Cation Source This example shows that $Ce^{3+}$ ions can effectively fragment HIV-1 amplicons which are labeled in the same reaction mixture with a fluorescent marker, providing nucleic acid fragments for detection on a DNA chip. The amplicons of HIV-1 protease sequence were prepared as described in Example 1. For fragmentation and labeling the reaction included 50 µl HIV-1 RNA amplicons, 125 µl imidazole buffer (0.1 M), 125 µl of CeCl₃ (100 mM), 6.25 µl of 5-(bromomethyl)fluorescein (10 mM in DMSO), and pure water to obtain a final reaction volume of 250 µl. The solution was mixed and incubated at 60° C. for 30 min. Then the reaction product was hybridized, detected and analyzed on an HIV-1 DNA chip as described in Example 2.

The results show that base calling was 98.1% for a median signal of 1656 RFU, with a background of 390 RFU, providing a S/B ratio of 4.2. Thus, use of CeCl₃ allows effective fragmentation and labeling by 5-(bromomethyl) fluorescein.

EXAMPLE 12

Labeling Using Different Metal Cation and Labeling Agent Concentrations

This example shows that effective labeling concomitant with fragmentation can be achieved using reduced concentration of the labeling agent relative to previous examples. In these assays, $Mn^{2+}$ was the metal ion. By simultaneously varying the concentrations of labeling agent, metal cation, imidazole and the pH, optimal conditions for fragmentation and labeling using different concentrations of reagents were discovered, using labeling agent in the range of 0.3 mM to 1.0 mM. When efficient labeling is achieved using less labeling agent in the reaction mixture, excess unattached labeling agent is decreased in the resulting product, thus reducing the need for post-labeling purification.

The nucleic acid labeled was 16S rRNA amplicons, prepared using TMA as described in Example 1. Each reaction included: 50 pi of RNA amplicons, imidazole buffer, MnCl₂, 5-bromomethyl)fluorescein (dissolved in DMF), with pure water added to obtain a final reaction volume of 100 µl. The concentrations of imidazole ("Im") and pH, MnCl₂ ("$Mn^{2+}$") and 5 (bromomethyl)fluorescein ("5-BMF") were varied as shown in the Table 8. The solution was mixed and incubated at 60° C. for 30 min.

Following labeling, the reaction product was hybridized, detected and analyzed on the *Mycobacterium* DNA chip described in Example 2, except that the hybridization buffer contained 60 mM HEPES, pH 7.0 in place of the phosphate buffer.

TABLE 8

Labeling Results Obtained with Different Labeling Reaction Formulations

| Im, pH | Mn$^{2+}$ | 5-BMF | BC % | Signal RFU | Background RFU | S/B |
|---|---|---|---|---|---|---|
| 30 mM pH 6.8 | 30 mM | 0.55 mM | 96.8 | 3308 | 878 | 3.8 |
| 30 mM pH 6.8 | 60 mM | 0.1 mM | 93.5 | 1059 | 395 | 2.7 |
| 30 mM pH 6.8 | 30 mM | 0.55 mM | 97.8 | 3272 | 881 | 3.7 |
| 30 mM pH 6.8 | 30 mM | 1.0 mM | 98.4 | 4270 | 1279 | 3.3 |
| 15 mM pH 7.2 | 45 mM | 0.3 mM | 96.2 | 2085 | 633 | 3.3 |
| 15 mM pH 7.2 | 15 mM | 0.3 mM | 94.1 | 1696 | 523 | 3.2 |

These results show that efficient labeling of detectable nucleic acid fragments was achieved even at relatively low (0.3 mM) concentration of labeling agent, while maintaining a relatively constant S/B compared to the results obtained using higher labeling agent concentrations (0.55 to 1.0 mM).

EXAMPLE 13

Fragmentation and Labeling as a Decontamination Tool

TMA reactions were performed as described in Example 1. Fragmentation and labeling reactions were performed in a plastic tube using 100 μl of TMA amplicons from *M. tuberculosis* target with the conditions described in Example 2 except that an upper layer of inert silicon oil was included in the reaction mixture. Following fragmentation and labeling, the reaction mixture was extracted with 2400 μl of 1-butanol (water saturated), as described in Example 2. Following separation of the aqueous and organic layers, TMA reactions were performed using 5 μl from each layer, and using the same volume containing unlabeled target as a positive control. While the 20 unlabeled target gave the expected amplification product, no amplicons were detected in the TMA reactions that used aliquots of either the aqueous or organic layers. These results show that the fragments produced during the fragmentation and labeling reaction cannot be amplified under these conditions. Thus the fragmentation and labeling process can serve as a decontamination procedure.

What is claimed is:

1. A process for fragmenting and labeling at least one synthetic or natural DNA, RNA or chimeric DNA-RNA polymer, comprising the steps of:
obtaining a mixture in which the at least one DNA, RNA or chimeric DNA-RNA polymer has been subject to an in vitro nucleic acid amplification reaction;
chemically fragmenting the at least one DNA, RNA or chimeric DNA RNA polymer in the mixture in the presence of at least one multivalent metal cation in an aqueous solution, to produce a plurality of DNA or RNA fragments having freed terminal phosphates for further reaction; and
attaching a labeling agent on a plurality of said fragments at freed terminal phosphates located at the 3' end and/or 5' end of said fragments, wherein the fragmenting and attaching steps take place in an in vitro nucleic acid amplification mixture.

2. A process for fragmenting and labeling a synthetic or natural DNA or RNA nucleic acid, comprising the steps of:
obtaining a mixture in which the DNA or RNA nucleic acid has been subject to an in vitro nucleic acid amplification reaction;
chemically fragmenting said nucleic acid in the mixture in the presence of at least one multivalent metal cation in an aqueous solution, to produce a plurality of DNA or RNA fragments having freed terminal phosphates for further reaction;
attaching a labeling agent on a plurality of said fragments at freed terminal phosphates located at the 3' end and/or 5' end of said fragments; and
treating said mixture to decrease or eliminate unattached labeling agent, wherein the treating step physically separates the labeled nucleic acid fragment from unattached labeling agent in the mixture after the fragmenting and attaching steps, and wherein the treating step dilutes the mixture.

3. The process according to claim 1, further comprising a treating step that physically separates labeled nucleic acid fragments from unattached labeling agent after the fragmenting and attaching steps.

4. The process according to claim 3, wherein the treating step uses an organic solvent to separate the labeled nucleic acid fragment from the unattached labeling agent.

5. The process according to claim 3, wherein the treating step separates a labeled nucleic acid fragment from unattached labeling agent by using solid phase extraction of the labeled nucleic acid fragment on a solid support.

6. The process according to claim 3, wherein the treating step precipitates a labeled nucleic acid fragment at ambient temperature from the mixture that further contains betaine, dodecyl trimethylammonium bromide (DTAB) and unlabeled nucleic acid.

7. The process according to claim 1, wherein the fragmenting and attaching steps are effected in separate steps.

8. The process according to claim 1, wherein the DNA, RNA, or chimeric DNA-RNA polymer comprises at least one thiophosphate nucleotide.

9. The process according to claim 8, wherein the fragmenting step for RNA or chimeric DNA-RNA polymer comprising at least one thiophosphate nucleotide is performed in the presence of at least one multivalent metal cation selected from the group consisting of $Sr^{2+}$, $Ba^{2+}$, $Pb^{2+}$, $Cd^{2+}$, $Fe^{2+}$, $Ni^{2+}$, $Ru^{3+}$, $Ce^{3+}$, $Eu^{3+}$, $Tb^{3+}$, $Tm^{3+}$, $Yb^{3+}$, and $Lu^{3+}$ and a chemical catalyst.

10. The process according to claim 8, wherein the fragmenting step for RNA or chimeric DNA-RNA polymer comprising at least one thiophosphate nucleotide is performed in the presence of at least one multivalent metal cation selected from the group consisting of $Cr^{3+}$, $Ce^{3+}$, $Yb^{3+}$, $Tb^{3+}$, $Eu^{2+}$ and $Pb^{2+}$.

11. The process according to claim 8, wherein the fragmenting step for RNA or chimeric DNA-RNA polymer comprising at least one thiophosphate nucleotide is performed in the presence of at least one multivalent metal cation selected from the group consisting of $Be^{2+}$, $Cr^{3+}$, $Pb^{2+}$, $In^{3+}$, $Tb^{3+}$, $Ce^{3+}$, $Yb^{3+}$ and $Ni^{2+}$.

12. The process according to claim 1, wherein the attaching step attaches a label to an internal or terminal thiophosphate nucleotide.

13. The process according to claim 1, wherein the fragmenting step further includes use of a chemical catalyst.

14. The process according to claim 13, wherein the chemical catalyst is selected from the group consisting of imidazole, a substituted analogue of imidazole and a compound that includes an imidazole ring or a substituted analogue of an imidazole ring.

15. The process according to claim 13, wherein the chemical catalyst is selected from the group consisting of N-methylimidazole, 3-(N-morpholino) propane sulfonic acid (MOPS), N'-2-hydroxyethylpiperazine-N'-2-ethanesulfonic acid (HEPES), piperazine-N,N'-bis(2-ethane sulfonic acid) (PIPES) and bioorganic polyamines.

16. The process according to claim 1, wherein the fragmenting step for RNA or chimeric DNA-RNA polymer is performed in the presence of at least one multivalent metal cation selected from the group consisting of $Sr^{2+}$, $Ba^{2+}$, $Pb^{2+}$, $Cd^{2+}$, $Fe^{2+}$, $Ni^{2+}$, $Ru^{3+}$, $Ce^{3+}$, $Eu^{3+}$, $Tb^{3+}$, $Tm^{3+}$, $Yb^{3+}$ and $Lu^{3+}$ and a chemical catalyst.

17. The process according to claim wherein the fragmenting step for RNA or chimeric DNA-RNA polymer is performed in the presence of at least one multivalent metal cation selected from the group consisting of $Cr^{3+}$, $Ce^{3+}$, $Yb^{3+}$, $Tb^{3+}$, $Eu^{2+}$ and $Pb^{2+}$.

18. The process according to claim 1, wherein the fragmenting step for DNA or chimeric DNA-RNA polymer is performed in the presence of $Tb^{3+}$ and a chemical catalyst.

19. The process according to claim 1, wherein the fragmenting step for DNA or chimeric DNA-RNA polymer is performed in the presence of at least one multivalent metal cation selected from the group consisting of $Be^{2+}$, $Cr^{3+}$, $Pb^{2+}$, $In^{3+}$, $Ce^{3+}$, $Yb^{3+}$ and $Ni^{2+}$.

20. The process according to claim 1, wherein the multivalent metal cation is selected from the group consisting of $Tb^{3+}$ and $Ce^{3+}$.

21. The process according to claim 1, wherein the mixture contains the labeling agent in a concentration of from 0.1 mM to 4 mM.

22. The process according to claim 21, wherein the mixture contains the labeling agent in a concentration of from 0.1 mM to 1 mM.

23. The process according to claim 21, wherein the mixture contains the labeling agent in a concentration of from 0.3 mM to 0.55 mM.

24. The process according to claim 1, wherein the labeling agent contains alkyl halide or haloacetamide reactive functions.

25. The process according to claim 1, wherein the labeling agent is selected from the group consisting of 5-(bromomethyl)fluoroscein, 6-(bromomethyl)fluorescein, 6-iodoacetamidofluorescein and 5-iodoacetamidofluorescein.

26. The process according to claim 2, wherein the treating step further includes adding an acid to the aqueous solution after the fragmenting and attaching steps.

27. The process according to claim 2, wherein the treating step uses an organic solvent to separate the labeled nucleic acid fragment from the unattached labeling agent.

28. The process according to claim 27, wherein the organic solvent is selected from the group consisting of 1-butanol, 2-butanol, isopentyl alcohol, 1-pentanol and cyclohexanol.

29. The process according to claim 2, wherein the treating step separates a labeled nucleic acid fragment from unattached labeling agent by using solid phase extraction of the labeled nucleic acid fragment on a solid support.

30. The process according to claim 29, wherein said solid support is selected from the group consisting of beads, gels, ion exchange resin, reverse phase resin, silica matrix and a membrane.

31. The process according to claim 29, wherein the labeled nucleic acid fragment is eluted from the solid support by using a buffer containing betaine.

32. The process according to claim 2, wherein the treating step precipitates the labeled nucleic acid fragment at ambient temperature from the aqueous solution that further contains betaine, dodecyl trimethylammonium bromide (DTAB) and unlabeled nucleic acid.

33. The process according to claim 2, wherein the treating step comprises adding a quencher to the aqueous solution after the fragmenting and attaching steps.

34. The process according to claim 33, wherein the quencher is selected from the group consisting of pyrophosphate, thiol derivative, chelating agent, phosphate anion and carbonate anion.

35. The process according to claim 2, wherein the fragmenting and attaching steps are effected in separate steps.

36. The process according to claim 2, wherein the DNA or RNA nucleic acid comprises at least one thiophosphate nucleotide.

37. The process according to claim 36, wherein the RNA nucleic acid comprising at least one thiophosphate nucleotide is chemically fragmented in the presence of at least one multivalent metal cation selected from the group consisting of $Sr^{2+}$, $Ba^{2+}$, $Pb^{2+}$, $Cd^{2+}$, $Fe^{2+}$, $Ni^{2+}$, $Ru^{3+}$, $Ce^{3+}$, $Eu^{3+}$, $Tb^{3+}$, $Tm^{3+}$, $Yb^{3+}$ and $Lu^{3+}$ and a chemical catalyst.

38. The process according to claim 36, wherein the RNA nucleic acid comprising at least one thiophosphate nucleotide is chemically fragmented in the presence of at least one multivalent metal cation selected from the group consisting of $Cr^{3+}$, $Ce^{3+}$, $Yb^{3+}$, $Tb^{3+}$, $Eu^{2+}$ and $Pb^{2+}$.

39. The process according to claim 36, wherein the DNA nucleic acid comprising at least one thiophosphate nucleotide is chemically fragmented in the presence of at least one multivalent metal cation selected from the group consisting of $Be^{2+}$, $Cr^{3+}$, $Pb^{2+}$, $In^{3+}$, $Tb^{3+}$, $Yb^{3+}$ $Ni^{2+}$.

40. The process according to claim 2, wherein the RNA nucleic acid is chemically fragmented in the presence of at least one multivalent metal cation selected from the group consisting of $Sr^{2+}$, $Ba^{2+}$, $Pb^{2+}$, $Cd^{2+}$, $Fe^{2+}$, $Ni^{2+}$, $Ru^{3+}$, $Ce^{3+}$, $Eu^{3+}$, $Tb^{3+}$, $Tm^{3+}$, $Yb^{3+}$ and $Lu^{3+}$ and a chemical catalyst.

41. The process according to claim 2, wherein the RNA nucleic acid is chemically fragmented in the presence of at least one multivalent metal cation selected from the group consisting of $Cr^{3+}$, $Ce^{3+}$, $Yb^{3+}$, $Tb^{3+}$, $Eu^{2+}$ and $Pb^{2+}$.

42. The process according to claim 2, wherein the DNA nucleic acid is chemically fragmented in the presence of $Tb^{3+}$ and a chemical catalyst.

43. The process according to claim 2, wherein the DNA nucleic acid is chemically fragmented in the presence of at least one multivalent metal cation selected from the group consisting of $Be^{2+}$, $Cr^{3+}$, $Pb^{2+}$, $In^{3+}$, $Tb^{3+}$, $Ce^{3+}$, $Yb^{3+}$ and $Ni^{2+}$.

44. The process according to claim 2, wherein the multivalent metal cation is selected from the group consisting of $Tb^{3+}$ and $Ce^{3+}$.

45. The process according to claim 2, wherein the aqueous solution contains the labeling agent in a concentration of from 0.1 mM to 4 mM.

46. The process according to claim 45, wherein the aqueous solution contains the labeling agent in a concentration of from 0.1 mM to 1 mM.

47. The process according to claim 45, wherein the aqueous solution contains the labeling agent in a concentration of from 0.3 mM to 0.55 mM.

48. The process according to claim 2, wherein the labeling agent contains alkyl halide or haloacetamide reactive functions.

49. The process according to claim 2, wherein the labeling agent is selected from the group consisting of 5-(bromomethyl)fluoroscein, 6-(bromomethyl)fluorescein, 6-iodoacetamidofluorescein and 5-iodoacetamidofluorescein.

* * * * *

UNITED STATES PATENT AND TRADEMARK OFFICE
CERTIFICATE OF CORRECTION

PATENT NO. : 6,902,891 B2
DATED : June 7, 2005
INVENTOR(S) : Ali Laayoun et al.

It is certified that error appears in the above-identified patent and that said Letters Patent is hereby corrected as shown below:

Column 30,
Line 63, should read -- The process according to claim 1 wherein the fragment- --.

Column 32,
Line 22, should read -- of $Be^{2+}$, $Cr^{3+}$, $Pb^{2+}$, $In^{3+}$, $Tb^{3+}$, $Ce^{3+}$, $Yb^{3+}$ and $Ni^{2+}$ --.

Signed and Sealed this

Sixteenth Day of August, 2005

JON W. DUDAS
*Director of the United States Patent and Trademark Office*